US009445921B2

(12) United States Patent
McLean

(10) Patent No.: US 9,445,921 B2
(45) Date of Patent: *Sep. 20, 2016

(54) DEVICE FOR EXPANDING AND SUPPORTING BODY TISSUE

(71) Applicant: SPINE WAVE, INC., Shelton, CT (US)

(72) Inventor: Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/736,689

(22) Filed: Jun. 11, 2015

(65) Prior Publication Data

US 2015/0282943 A1    Oct. 8, 2015

Related U.S. Application Data

(63) Continuation-in-part of application No. 14/474,555, filed on Sep. 2, 2014, now Pat. No. 9,078,767.

(60) Provisional application No. 61/948,645, filed on Mar. 6, 2014.

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/8858* (2013.01); *A61F 2/4455* (2013.01);
(Continued)

(58) Field of Classification Search
CPC .. A61F 2/44; A61F 2/442; A61F 2002/4435; A61F 2/445; A61F 2/4475
USPC ............... 606/246–249; 623/17.11–17.16
See application file for complete search history.

(56) References Cited

U.S. PATENT DOCUMENTS

| 3,486,505 A | 12/1969 | Morrison |
| 4,524,766 A | 6/1985 | Petersen |

(Continued)

FOREIGN PATENT DOCUMENTS

| EP | 0621020 A1 | 10/1994 |
| FR | 2639823 A1 | 6/1990 |

(Continued)

OTHER PUBLICATIONS

PCT Search Report for corresponding PCT Application No. PCT/US2008/064534.

(Continued)

*Primary Examiner* — Ellen C Hammond
*Assistant Examiner* — Christina Negrellirodrigue
(74) *Attorney, Agent, or Firm* — Hoffmann & Baron, LLP

(57) ABSTRACT

An expandable device for expanding and supporting body tissue comprises an inferior endplate having an outer surface configured to contact one body tissue surface and a superior endplate having an outer surface configured to contact an opposing body tissue surface. The inferior endplate and the superior endplate are movable relative to each other in a direction of expansion. The device includes an elevator captively supported between the inferior endplate and the superior endplate for independent movement along the direction of expansion. In the first direction the elevator is moved toward said superior endplate to lift the superior endplate and expand the device. In the second direction the elevator moves away from said superior endplate toward said inferior endplate to create a space for insertion of an insert into the expanded device.

33 Claims, 30 Drawing Sheets

(51) Int. Cl.
*A61B 17/88* (2006.01)
*A61F 2/30* (2006.01)

(52) U.S. Cl.
CPC ...... *A61F2/4611* (2013.01); *A61F 2002/3008* (2013.01); *A61F 2002/30131* (2013.01); *A61F 2002/30166* (2013.01); *A61F 2002/30401* (2013.01); *A61F 2002/30556* (2013.01); *A61F 2002/30579* (2013.01); *A61F 2002/30599* (2013.01); *A61F 2002/30601* (2013.01); *A61F 2002/30784* (2013.01); *A61F 2002/30797* (2013.01); *A61F 2002/30904* (2013.01); *A61F 2002/4623* (2013.01); *A61F 2002/4627* (2013.01); *A61F 2310/00017* (2013.01); *A61F 2310/00023* (2013.01); *A61F 2310/00029* (2013.01); *A61F 2310/00239* (2013.01); *A61F 2310/00317* (2013.01)

(56) References Cited

U.S. PATENT DOCUMENTS

| | | | |
|---|---|---|---|
| 4,683,476 A | 7/1987 | Ferrari et al. | |
| 4,736,738 A | 4/1988 | Lipovsek et al. | |
| 4,743,493 A | 5/1988 | Sioshansi et al. | |
| 4,755,797 A | 7/1988 | Kanaya | |
| 4,863,476 A | 9/1989 | Shepperd | |
| 4,888,024 A | 12/1989 | Powlan | |
| 5,059,193 A | 10/1991 | Kuslich | |
| 5,192,326 A | 3/1993 | Bao et al. | |
| 5,192,327 A | 3/1993 | Brantigan | |
| 5,197,971 A | 3/1993 | Bonutti | |
| 5,298,254 A | 3/1994 | Prewett et al. | |
| 5,431,658 A | 7/1995 | Moskovich | |
| 5,439,684 A | 8/1995 | Prewett et al. | |
| 5,505,732 A | 4/1996 | Michelson | |
| 5,514,180 A | 5/1996 | Heggeness et al. | |
| 5,522,899 A | 6/1996 | Michelson | |
| 5,571,109 A | 11/1996 | Bertagnoli | |
| 5,591,235 A | 1/1997 | Kuslich | |
| 5,645,599 A | 7/1997 | Samani | |
| 5,702,454 A | 12/1997 | Baumgartner | |
| 5,755,797 A | 5/1998 | Baumgartner | |
| 5,756,127 A | 5/1998 | Grisoni et al. | |
| 5,766,252 A | 6/1998 | Henry et al. | |
| 5,836,948 A | 11/1998 | Zucherman et al. | |
| 5,860,977 A | 1/1999 | Zucherman et al. | |
| 5,891,147 A | 4/1999 | Moskovitz et al. | |
| 5,951,553 A | 9/1999 | Betz et al. | |
| 5,980,522 A | 11/1999 | Koros et al. | |
| 6,033,411 A | 3/2000 | Preissman | |
| 6,045,579 A | 4/2000 | Hochshuler et al. | |
| 6,066,154 A | 5/2000 | Reiley et al. | |
| 6,074,390 A | 6/2000 | Zucherman et al. | |
| 6,110,179 A | 8/2000 | Flivik et al. | |
| 6,110,210 A | 8/2000 | Norton et al. | |
| 6,159,211 A | 12/2000 | Boriani et al. | |
| 6,159,244 A | 12/2000 | Suddaby | |
| 6,183,517 B1 | 2/2001 | Suddaby | |
| 6,190,414 B1 | 2/2001 | Young et al. | |
| 6,200,347 B1 | 3/2001 | Anderson et al. | |
| 6,241,771 B1 | 6/2001 | Gresser et al. | |
| 6,273,916 B1 | 8/2001 | Murphy | |
| 6,279,916 B1 | 8/2001 | Stecher | |
| 6,287,308 B1 | 9/2001 | Betz et al. | |
| 6,287,309 B1 | 9/2001 | Baccelli et al. | |
| 6,290,724 B1 | 9/2001 | Marino | |
| 6,387,130 B1 | 5/2002 | Stone et al. | |
| 6,395,034 B1 | 5/2002 | Suddaby | |
| 6,402,750 B1 | 6/2002 | Atkinson et al. | |
| 6,419,705 B1 | 7/2002 | Erickson | |
| 6,432,107 B1 | 8/2002 | Ferree | |
| 6,436,142 B1 | 8/2002 | Paes et al. | |
| 6,478,800 B1 | 11/2002 | Fraser et al. | |
| 6,488,710 B2 | 12/2002 | Besselink | |
| 6,500,205 B1 | 12/2002 | Michelson | |
| 6,520,993 B2 | 2/2003 | James et al. | |
| 6,562,074 B2 | 5/2003 | Gerbec et al. | |
| 6,595,998 B2 | 7/2003 | Johnson et al. | |
| 6,620,196 B1 | 9/2003 | Trieu | |
| 6,648,917 B2 | 11/2003 | Gerbec et al. | |
| 6,656,178 B1 | 12/2003 | Sanders et al. | |
| 6,726,691 B2 | 4/2004 | Osorio et al. | |
| 6,740,093 B2 | 5/2004 | Hochshuler et al. | |
| 6,837,904 B2 | 1/2005 | Ralph et al. | |
| 6,852,095 B1 | 2/2005 | Ray | |
| 6,852,126 B2 | 2/2005 | Ahlgren | |
| 6,852,129 B2 | 2/2005 | Gerbec et al. | |
| 6,863,673 B2 | 3/2005 | Gerbec et al. | |
| 6,997,929 B2 | 2/2006 | Manzi et al. | |
| 7,118,580 B1 | 10/2006 | Beyersdorff et al. | |
| 7,329,283 B2 | 2/2008 | Estes et al. | |
| 7,591,852 B2 | 9/2009 | Prosser | |
| 7,722,625 B2 | 5/2010 | Sanders et al. | |
| 7,905,921 B2 | 3/2011 | Kim et al. | |
| 7,931,688 B2 | 4/2011 | Landry et al. | |
| 7,967,867 B2 | 6/2011 | Barreiro et al. | |
| 8,062,375 B2 | 11/2011 | Glerum et al. | |
| 8,303,663 B2 | 11/2012 | Jimenez et al. | |
| 8,303,879 B2 | 11/2012 | Bertele et al. | |
| 8,308,805 B2 | 11/2012 | Lynn et al. | |
| 8,337,562 B2 | 12/2012 | Landry et al. | |
| 8,382,842 B2 | 2/2013 | Greenhalgh et al. | |
| 8,585,761 B2 | 11/2013 | Theofilos | |
| 8,628,578 B2 | 1/2014 | Miller et al. | |
| 8,715,351 B1* | 5/2014 | Pinto | A61F 2/447 623/17.11 |
| 8,828,019 B1 | 9/2014 | Raymond et al. | |
| 8,900,312 B2 | 12/2014 | Mclean et al. | |
| 2002/0026195 A1 | 2/2002 | Layne et al. | |
| 2002/0147497 A1 | 10/2002 | Belef et al. | |
| 2002/0177897 A1 | 11/2002 | Michelson | |
| 2003/0171812 A1 | 9/2003 | Grunberg et al. | |
| 2004/0019354 A1 | 1/2004 | Johnson et al. | |
| 2004/0030387 A1 | 2/2004 | Landry et al. | |
| 2004/0064144 A1 | 4/2004 | Johnson et al. | |
| 2004/0220580 A1 | 11/2004 | Johnson et al. | |
| 2005/0027364 A1 | 2/2005 | Kim et al. | |
| 2005/0149194 A1 | 7/2005 | Ahlgren | |
| 2005/0283244 A1 | 12/2005 | Gordon et al. | |
| 2006/0058807 A1 | 3/2006 | Landry et al. | |
| 2006/0058880 A1 | 3/2006 | Wysocki et al. | |
| 2006/0129244 A1 | 6/2006 | Ensign | |
| 2008/0119853 A1 | 5/2008 | Felt et al. | |
| 2008/0154377 A1 | 6/2008 | Voellmicke | |
| 2008/0161927 A1 | 7/2008 | Savage et al. | |
| 2008/0172127 A1 | 7/2008 | Perez-Cruet et al. | |
| 2008/0300598 A1* | 12/2008 | Barreiro | A61F 2/4611 606/63 |
| 2009/0198339 A1 | 8/2009 | Kleiner et al. | |
| 2009/0306672 A1 | 12/2009 | Reindel et al. | |
| 2010/0312347 A1 | 12/2010 | Arramon et al. | |
| 2011/0184522 A1* | 7/2011 | Melkent | A61F 2/4611 623/17.16 |
| 2012/0022653 A1 | 1/2012 | Kirschman | |
| 2012/0158144 A1 | 6/2012 | Ullrich, Jr. et al. | |
| 2012/0191190 A1 | 7/2012 | Trieu | |
| 2013/0090735 A1 | 4/2013 | Mermuys et al. | |
| 2013/0184825 A1 | 7/2013 | Kleiner | |
| 2014/0364950 A1 | 12/2014 | Raymond et al. | |

FOREIGN PATENT DOCUMENTS

| | | |
|---|---|---|
| FR | 2719763 A1 | 11/1995 |
| WO | 9902214 A1 | 1/1999 |
| WO | 2013184946 A1 | 12/2013 |

OTHER PUBLICATIONS

Baddeley, S. and Cullen, J.C., "The Use of Methylmethacrylate in the Treatment of Giant Cell Tumours of the Proximal Tibia", Aust. N.Z. J. Surg. vol. 49—No. 1, Feb. 1979, 3 pp.

(56) References Cited

OTHER PUBLICATIONS

Campanacci, M., Gui, L., Ranieri, L., Savini, R., "Treatment of Tibial Plateau Fractures", Chi. Org. Mov. 72(3), Dec. 1975 (Italian text), pp. 234-256, English Translation, 15 pp.

Kyphon Inc., Surgical Technique Manual Nov. 16, 1999, pp. 5, 6, 9, 16-19.

Kyphon Vertebral Treatment Notebook, date unknown, 9 pp.

Kyphon web page, www.kyphon.com, Mar. 13, 2001, 1 p.

AOM Technique Manual, "Controlled Delivery for Osteoplasty, A Vertebroplasty Application", Cat #900.001—Rev B—date unknown.

Medtronic Sofamor Danek, "VERTE-STACK™, PEEK Stackable Corpectomy Device, Surgical Technique", date unknown, 8 pp.

Signus Medical, Tetris, Sep. 2003, 1 p.

Blackstone Medical Inc., Construx™ PEEK VBR System, 2005, www.blackstonemedical.com, 1 p.

Globus Medical, SUSTAIN™ R Small, date unknown, 6 pp.

\* cited by examiner

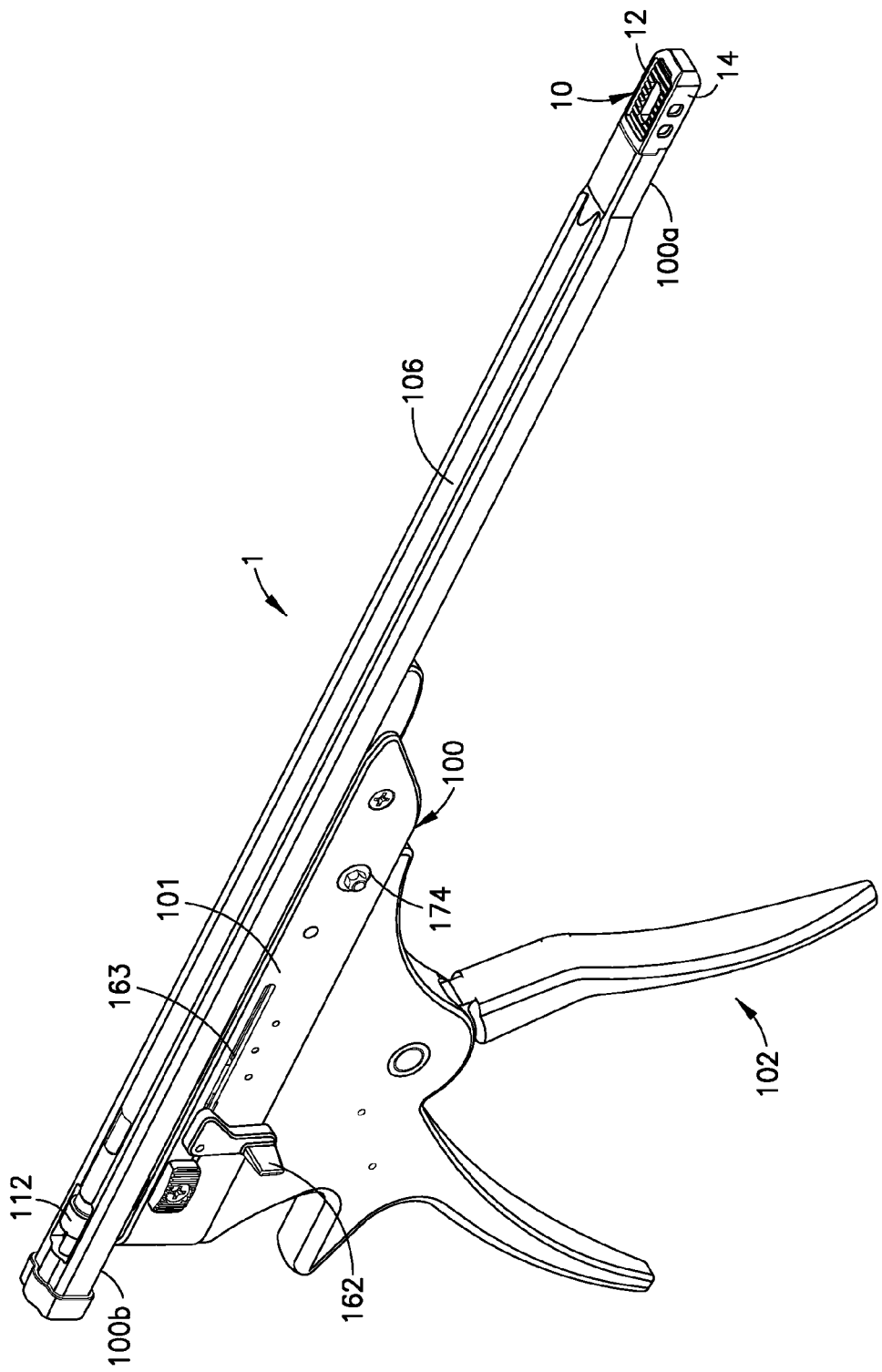

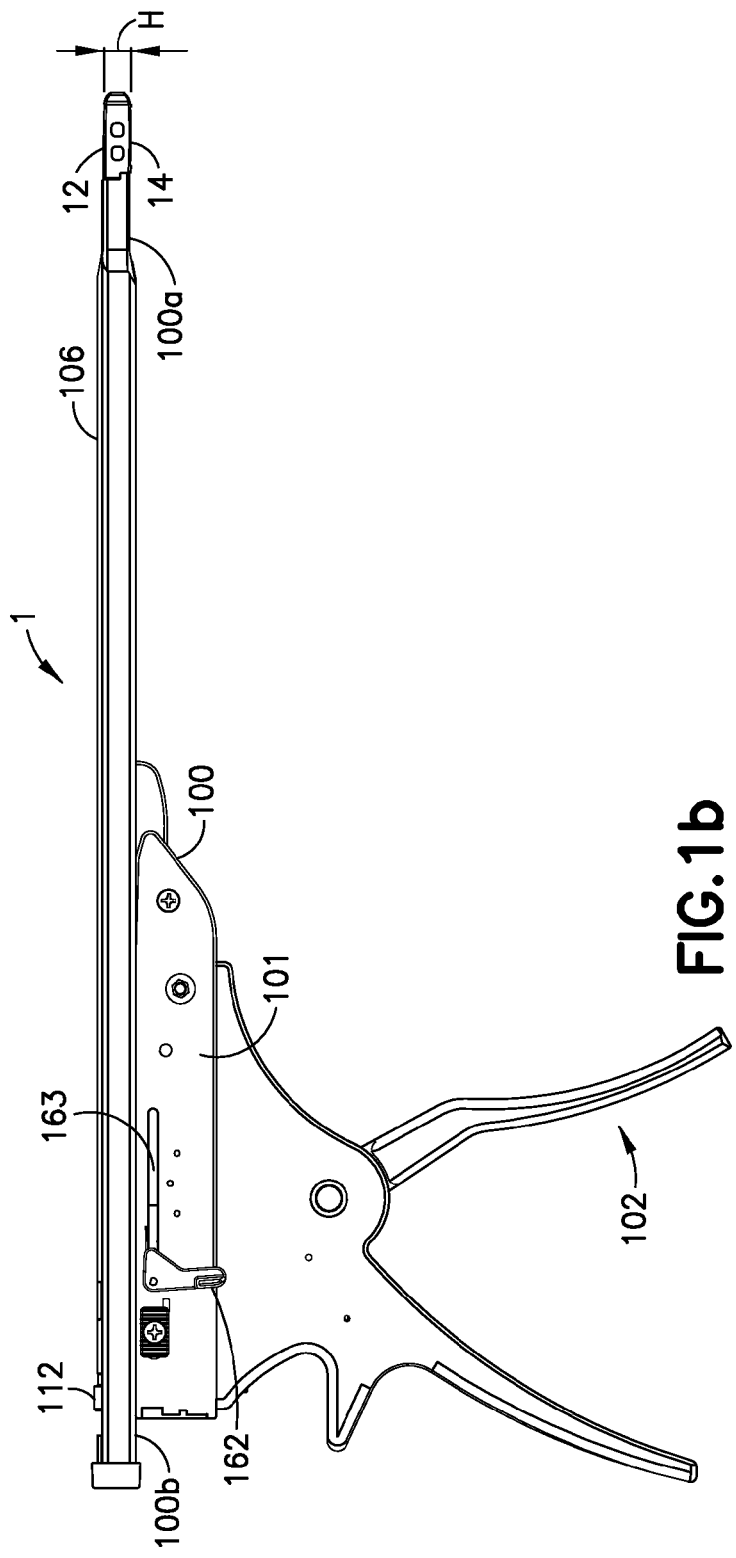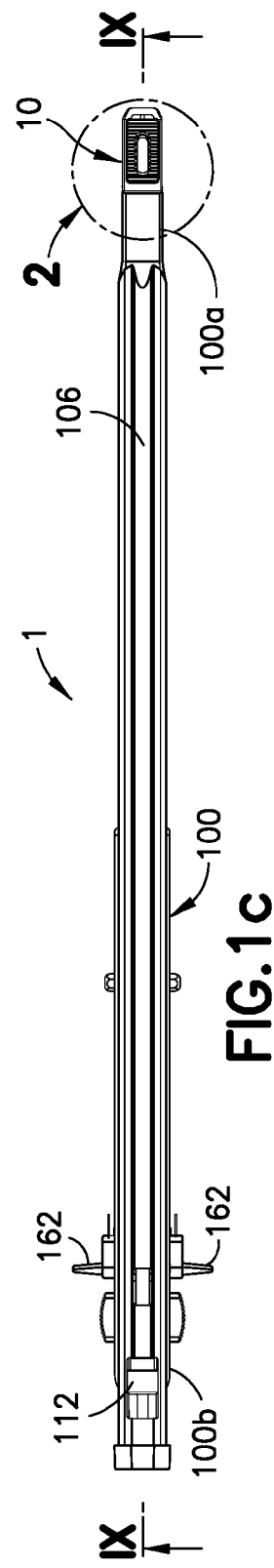

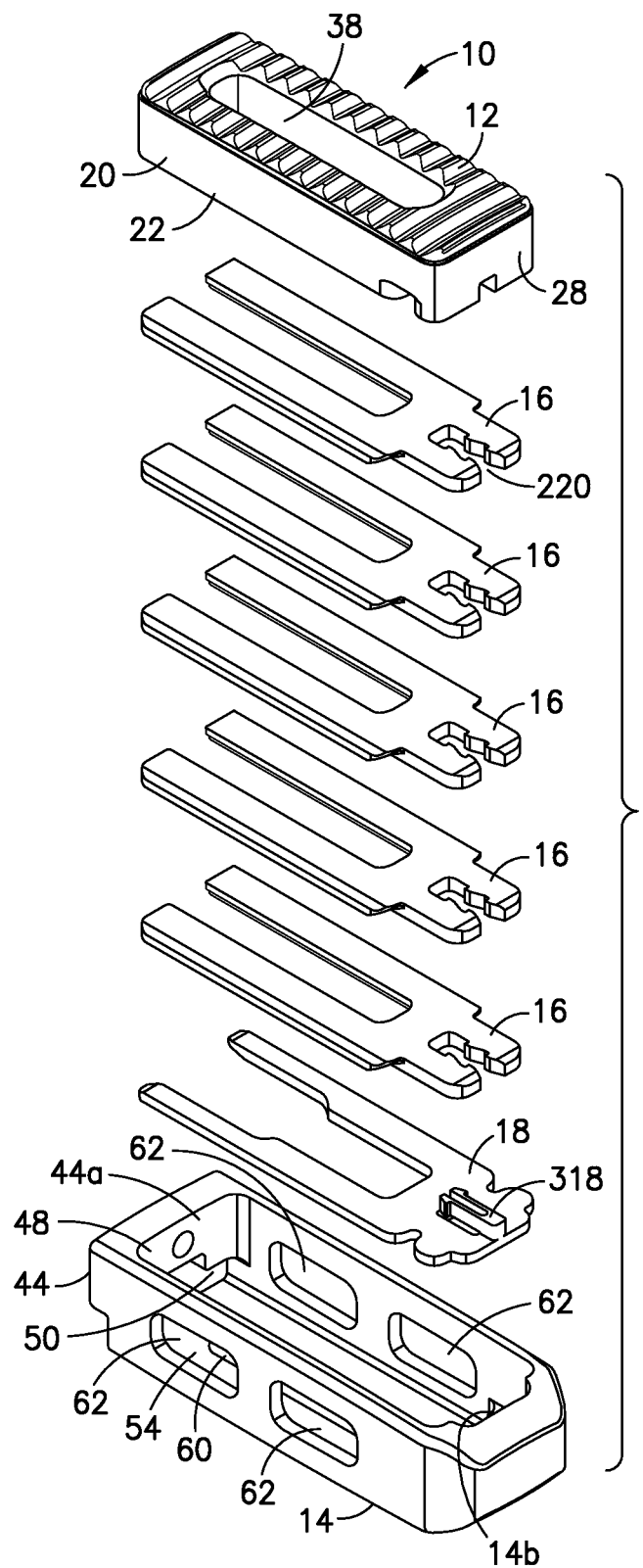

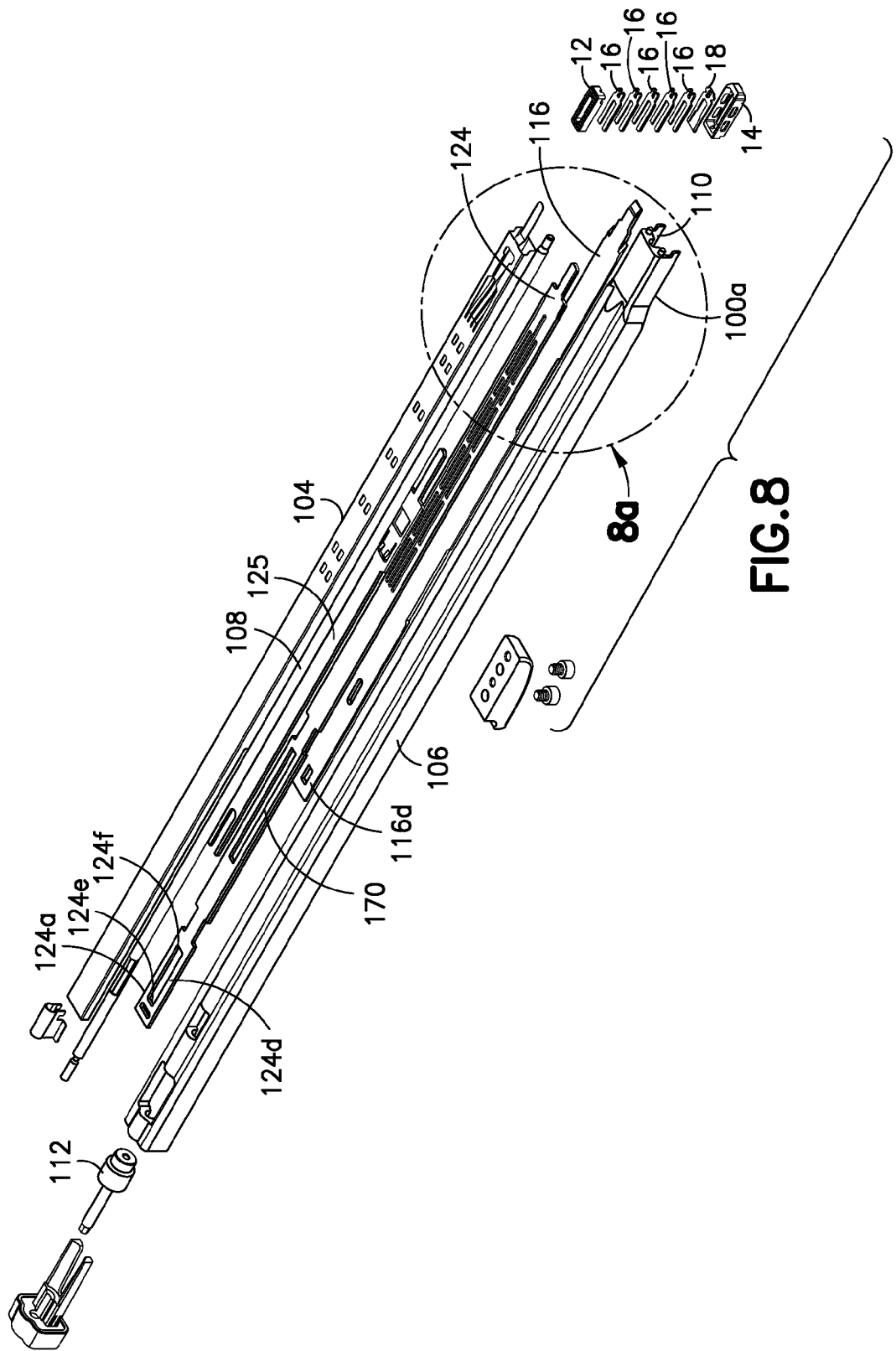

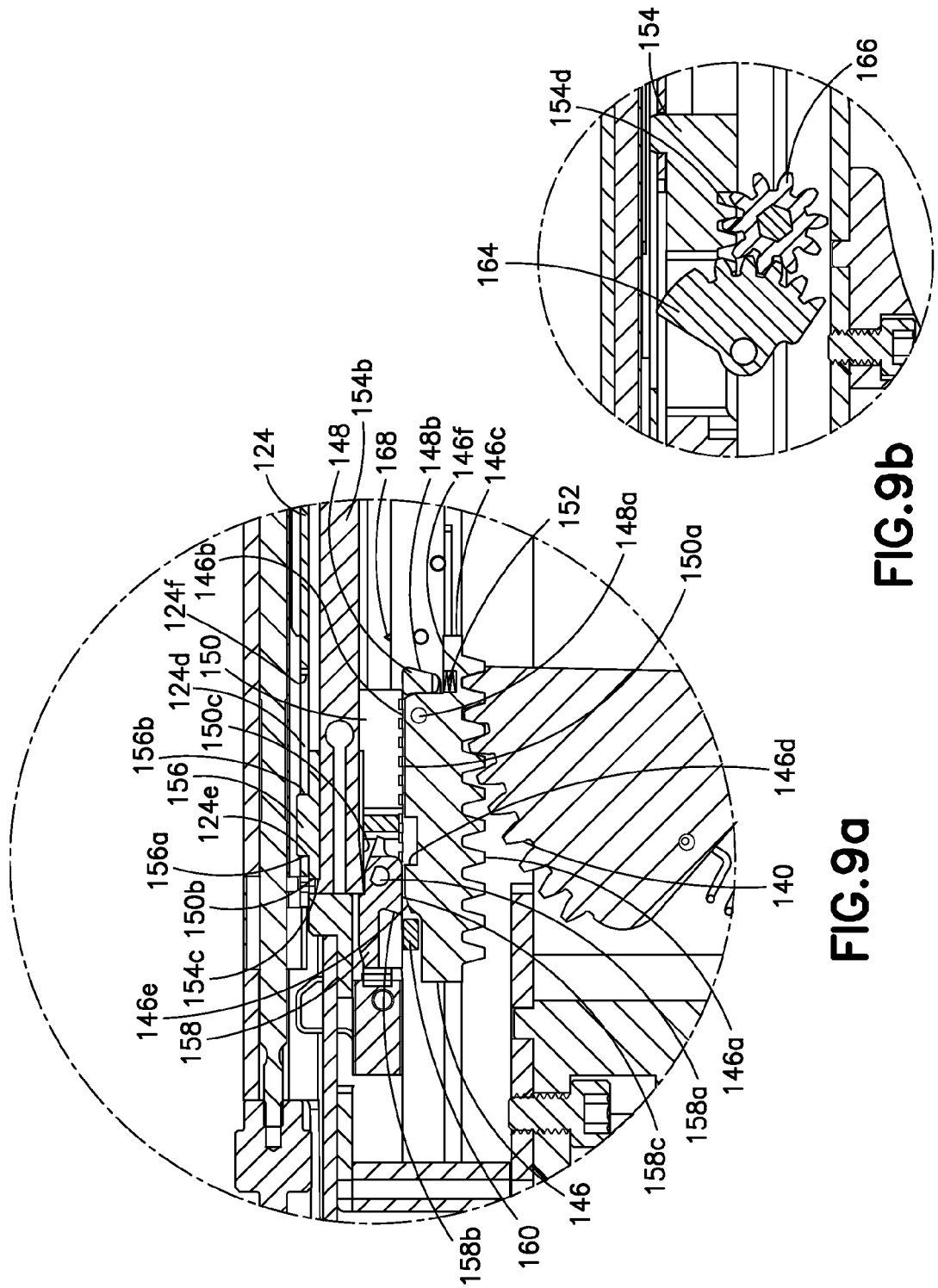

DEVICE FOR EXPANDING AND SUPPORTING BODY TISSUE

CROSS-REFERENCES TO RELATED APPLICATIONS

This is a continuation-in-part application of U.S. application Ser. No. 14/474,555, filed Sep. 2, 2014, now U.S. Pat. No. 9,078,767, which claims the benefit of U.S. Provisional Patent Application No. 61/948,645, filed Mar. 6, 2014, each of which is herein incorporated by reference in its entirety.

FIELD OF THE INVENTION

The subject invention relates generally to the field of surgery, and particularly to surgical devices, instruments and methods of using the same.

BACKGROUND OF THE INVENTION

A variety of physical conditions involves two bodily tissue surfaces that, for treatment of the condition, need to be separated from one another and supported away from one another. Such tissue expansion may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof.

One particular device for treating these conditions by distracting and supporting tissue surfaces simultaneously is described in U.S. Pat. No. 6,595,998, entitled "Tissue Distraction Device", which issued on Jul. 22, 2003 (the '998 patent). Other examples of such tissue distracting and supporting devices that are used for achieving spinal interbody fusion are described in U.S. Pat. No. 7,931,688 entitled "Expandable Interbody Fusion Device", which issued on Apr. 26, 2011 (the '688 patent), and U.S. Pat. No. 7,967,867 entitled "Expandable Interbody Fusion Device", which issued on Jun. 28, 2011 (the '867 patent). The '998 patent, the '688 patent and the '867 patent each discloses sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '998 patent, the '688 patent and the '867 patent are assigned to the same assignee as the present invention, the disclosures of these patents being incorporated herein by reference in their entirety.

An issue that has arisen regarding such interbody fusion devices that use inserts or wafers to incrementally expand such devices is the determination of when full expansion has been achieved as a result of ligamentotaxis and no further inserts may be inserted. It is therefore desirable for a surgeon to know when a sufficient number of inserts has been introduced to stabilize the spine and correct spinal height and whether any additional inserts may be introduced. One approach addressing this issue is described in commonly assigned U.S. Pat. No. 8,828,019, entitled "Inserter for Expanding an Expandable Interbody Fusion Device", issued on Sep. 9, 2014 ("the '019 patent") and incorporated herein by reference in its entirety.

Accordingly, in addition to interbody fusion applications, there is a similar need for other applications that use an expandable device and inserter to insert such a device into body tissue and expand the device in situ, including the capability to determine when proper expansion of the device has been achieved and no further inserts may be introduced.

SUMMARY OF THE INVENTION

It is an object of the invention to provide an improved device to expand body tissue and to introduce inserts after the device has been expanded. A further object is to provide an inserter that has the capability of allowing a surgeon to determine that suitable expansion has been reached and no additional inserts may be inserted.

DESCRIPTION OF THE FIGURES

FIG. 1a is a top perspective of an apparatus including an inserter releasably attached to an expandable spinal interbody fusion device in accordance with an embodiment of the present invention, the expandable interbody fusion device being unexpanded.

FIG. 1b is a side elevation view of the apparatus of FIG. 1a.

FIG. 1c is a top plan view of the apparatus of FIG. 1a.

FIG. 3a is top perspective view of the unexpanded fusion device of FIG. 1a.

FIG. 4 is an exploded top perspective view of the expanded device of FIG. 3b.

FIG. 5b is a sectional view of the device of FIG. 5a as seen along viewing lines B-B of FIG. 5a.

FIG. 5c is a sectional view of the device of FIG. 5a as seen along viewing lines C-C of FIG. 5a.

FIG. 6a is a top perspective view of an insert used in the expandable spinal interbody fusion device of FIG. 3a.

FIG. 6b is a top plan view of the insert of FIG. 6a.

FIG. 6d is a bottom plan view of the insert of FIG. 6a.

FIG. 6e is a distal end elevation view of the insert of FIG. 6a.

FIG. 7a is a top perspective view of an elevator used in the expandable spinal interbody fusion device of FIG. 3a.

FIG. 7b is a top plan view of the elevator of FIG. 7a.

FIG. 7d is a bottom plan view of the elevator of FIG. 7a.

FIG. 7e is a distal end elevation view of the elevator of FIG. 7a.

FIG. 8 is an exploded top perspective view of the track and components of the inserter of FIG. 1a, including the translatable lifting platform and translatable driver.

FIG. 9a is an enlarged view of the encircled portion A of FIG. 9.

FIG. 9b is an enlarged view of the encircled portion B of FIG. 9.

DESCRIPTION OF THE EMBODIMENTS

Figure 2:
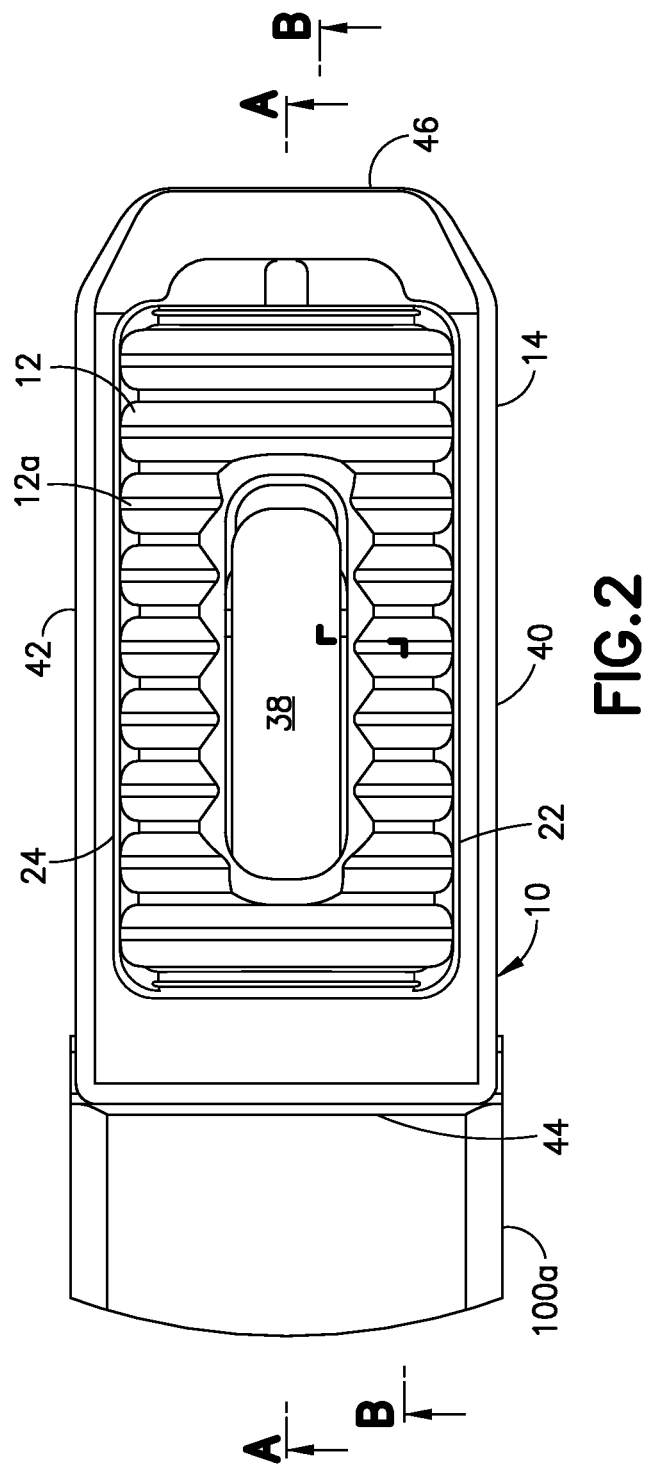
FIG. 2 is an enlarged view of the distal portion of the apparatus as circled in FIG. 1c.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3A:
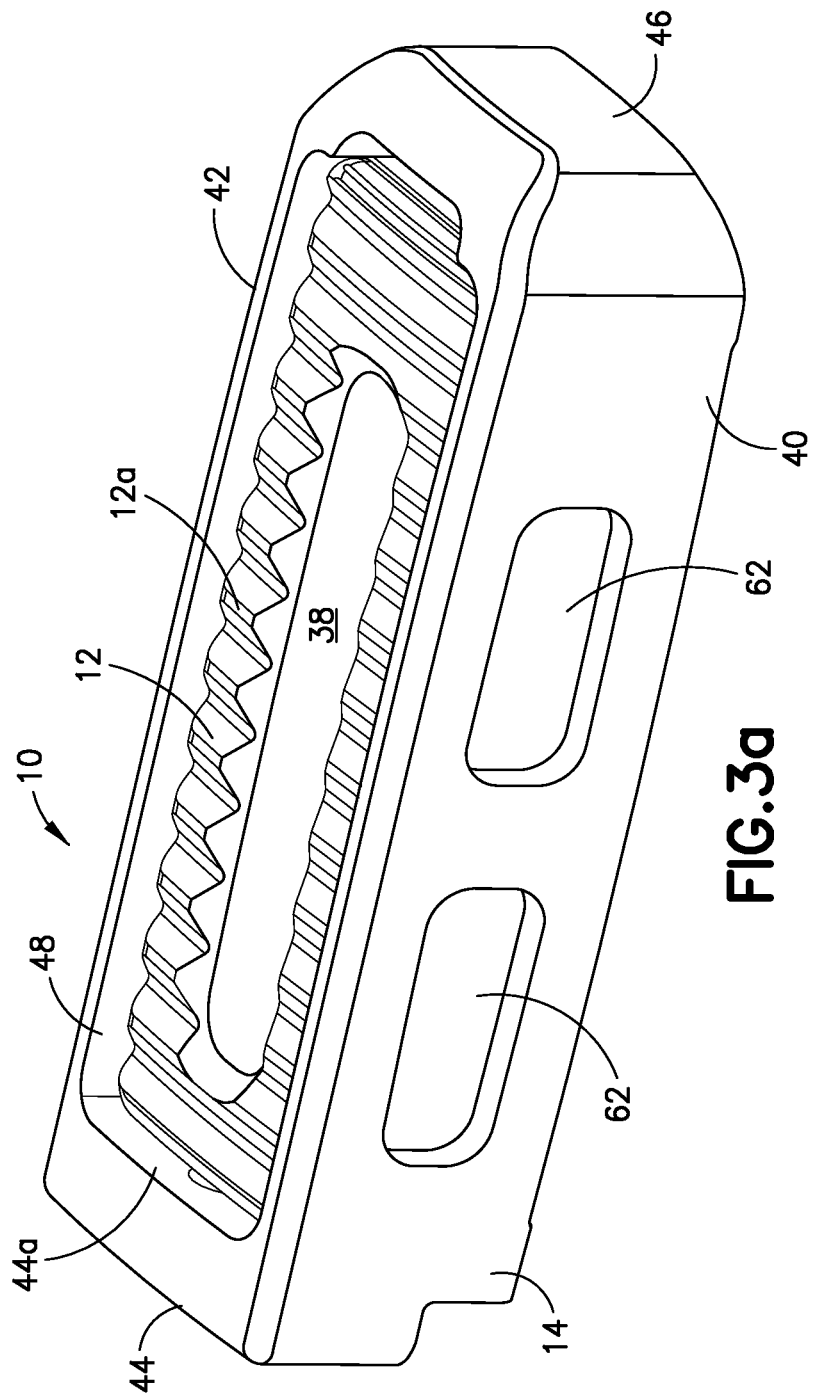
Figure 3B:
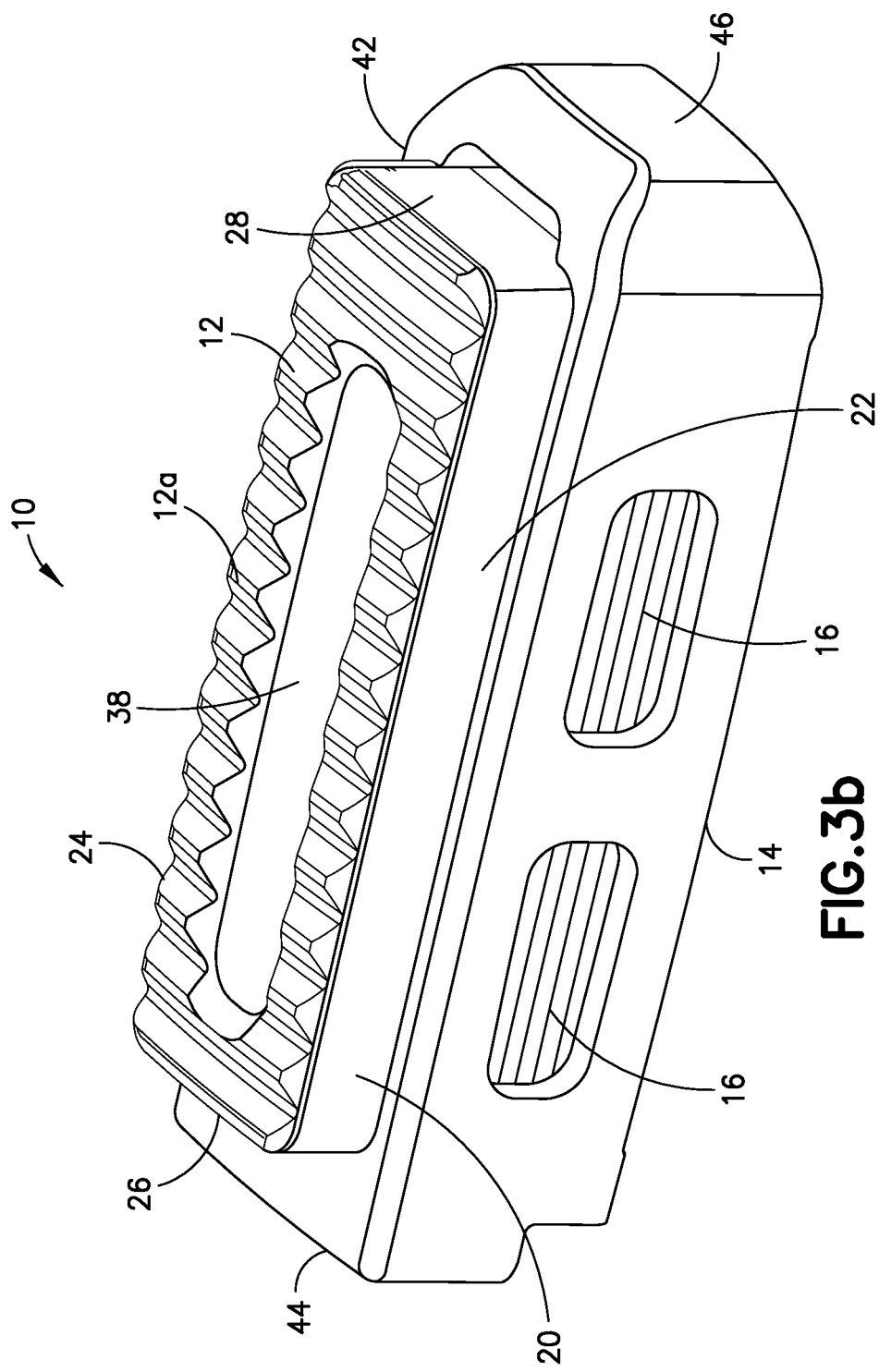
FIG. 3b is top perspective view of the fusion device of FIG. 3 after being expanded.

The invention provides a combination of an implantable expansion and support device and instrumentation to place the device into body tissue. The application of the invention as a spinal implant in spinal interbody fusion is detailed initially. Turning now to FIGS. 1a-c, 2, 3a-b and 4, an apparatus 1 for use in spinal interbody fusion is shown. Apparatus 1 comprises an expandable spinal interbody fusion device 10 and an inserter 100. The inserter 100 is an instrument used for inserting the device 10 into an intradiscal space between opposing vertebral bodies of a spine, expanding the device in situ and for inserting inserts into the expanded device 100. The expandable interbody fusion device 10 includes a first element, such as superior endplate 12, a second element, such as inferior endplate 14, at least one insert 16 and expansion structure including an elevator 18, as will be detailed hereinbelow. The height, H, across the superior and inferior endplates 12, 14 in the unexpanded condition as illustrated in FIG. 1b is less than the normal anatomic height of a typical intradiscal space. The invention contemplates expanding the interbody fusion device 10 by the inserter 100 from an unexpanded condition as shown in FIG. 3a to the expanded height as shown in FIG. 3b to ultimately restore the normal anatomic height of the disc space and thereafter inserting one or more inserts, such as inserts 16, as will be described, to form a stack of inserts 16 between the expanded superior endplate 12 and inferior endplate 14. In the particular arrangement being described, fusion device 10 is configured and sized for implantation into the spine from the posterior approach. In the unexpanded state as shown in FIG. 3a, device 10 has a length of approximately 25 mm, a width of approximately 10 mm, and an unexpanded height H of approximately 7 mm. Fusion device 10 may also be configured and sized for implantation into the spine using posteriolateral, anterior or lateral approaches, as will be described.

Figure 18:
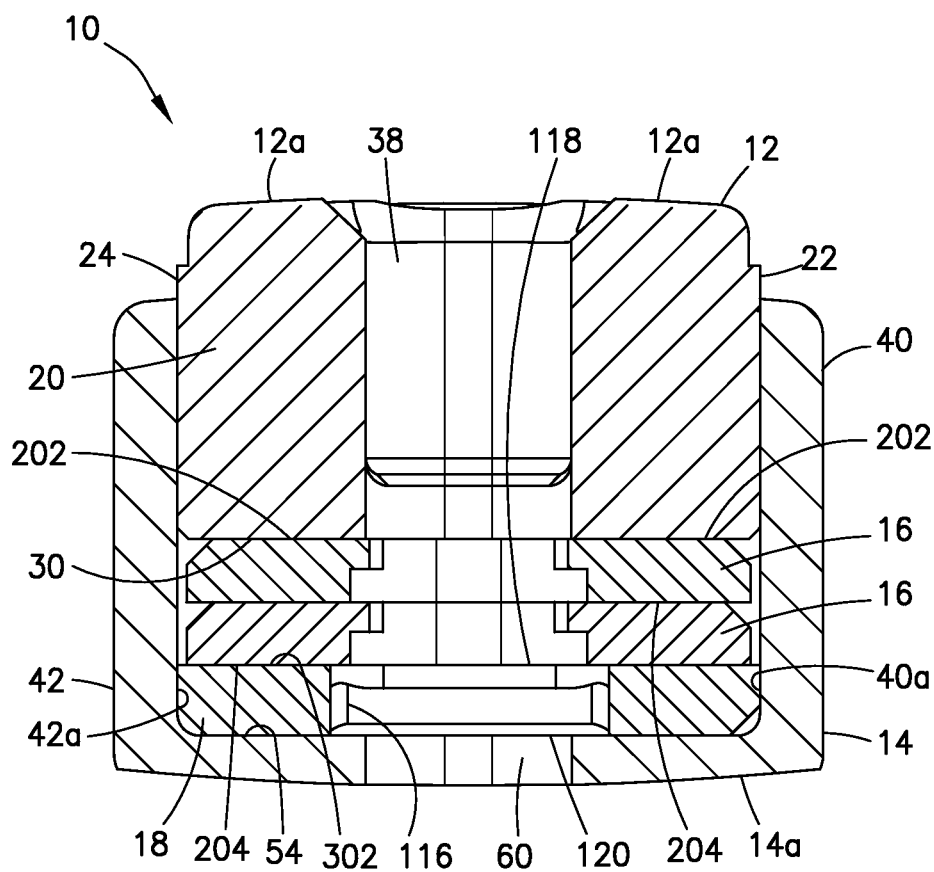
FIG. 18 is a cross-sectional view as seen along the viewing lines XVIII-XVIII of FIG. 17.

The superior endplate 12 as shown in FIGS. 3a-b and 18 is elongate and comprises a hub 20 having pair of side surfaces 22 and 24 extending longitudinally on each side of the hub 20 and a pair of end surfaces 26 and 28 extending respectively at the proximal rear end and the distal front end of the superior endplate 12. The hub 20 is sized and configured to fit within a cavity 48 of the inferior endplate 14 for telescoping movement therewithin, as will be described. The lower surface 30 of the hub 20 (FIG. 18) is generally flat and planar. Suitable friction or crush ribs may be provided between the hub 20 and cavity 48 of inferior endplate 14 at inner surface 44a to temporarily hold the superior and inferior endplates 12, 14 together in the direction of expansion as the device 10 is introduced into the intradiscal space to be distracted.

With continued reference to FIGS. 3a-b and 18, the superior endplate 12 includes a graft chamber defined by an opening 38 extending through the upper outer surface 12a and the lower surface 30. In accordance with one arrangement, the superior endplate 12 is formed of a biocompatible polymer such as polyethylethylketone (PEEK). PEEK is used in fusion applications for its combination of strength, biocompatibility, and elasticity which is similar to human bone. Other composites may include derivatives of PEEK such as carbon fiber reinforced PEEK and PEKK, respectively. In a particular aspect, the superior endplate 12 may further include an upper endcap that defines the outer surface 12a. The endcap may be a separate plate formed of material for the promotion of bone growth, such as titanium, and may be attached to the endplate 12 with suitable conventional techniques. As an alternative, the upper surface 12a may be defined by a coating of a suitable layer of bone growth promotion material, such as titanium, which may be deposited by conventional techniques.

The inferior endplate 14 of the interbody fusion device 10 as shown in FIGS. 3*a-b* and 18 is elongate and comprises a pair of opposing spaced apart sidewalls 40 and 42 extending along the longitudinal direction and projecting upwardly from the lower outer surface 14*a*. A pair of spaced apart end walls 44 and 46 extend laterally across the device 10 and project upwardly from outer surface 14*a*. Rear end wall 44 is disposed at the rear or proximal end of the device 10 and front end wall 46 is disposed at the front or distal end of the device 10. The side walls 40, 42 together with rear end wall 44 and front end wall 46 form an open, upwardly facing fully bounded interior cavity 48 as shown in FIGS. 3*a* and 4. The interior cavity 48 is sized and configured to receive the superior endplate 12 including the hub 20 in relatively close fit between the side walls 40 and 42 and the end walls 44 and 46 of the inferior endplate 14 in a non-expanded condition as shown in FIGS. 1*a-b*. The hub 20 of superior endplate 12, as well as the entire stack of inserts 16, remains fully contained within the inferior endplate 14 during telescoping expansion of the device 10 as shown in FIGS. 18 and 19, contributing to the torsional strength of the expanded device 10.

Figure 19:
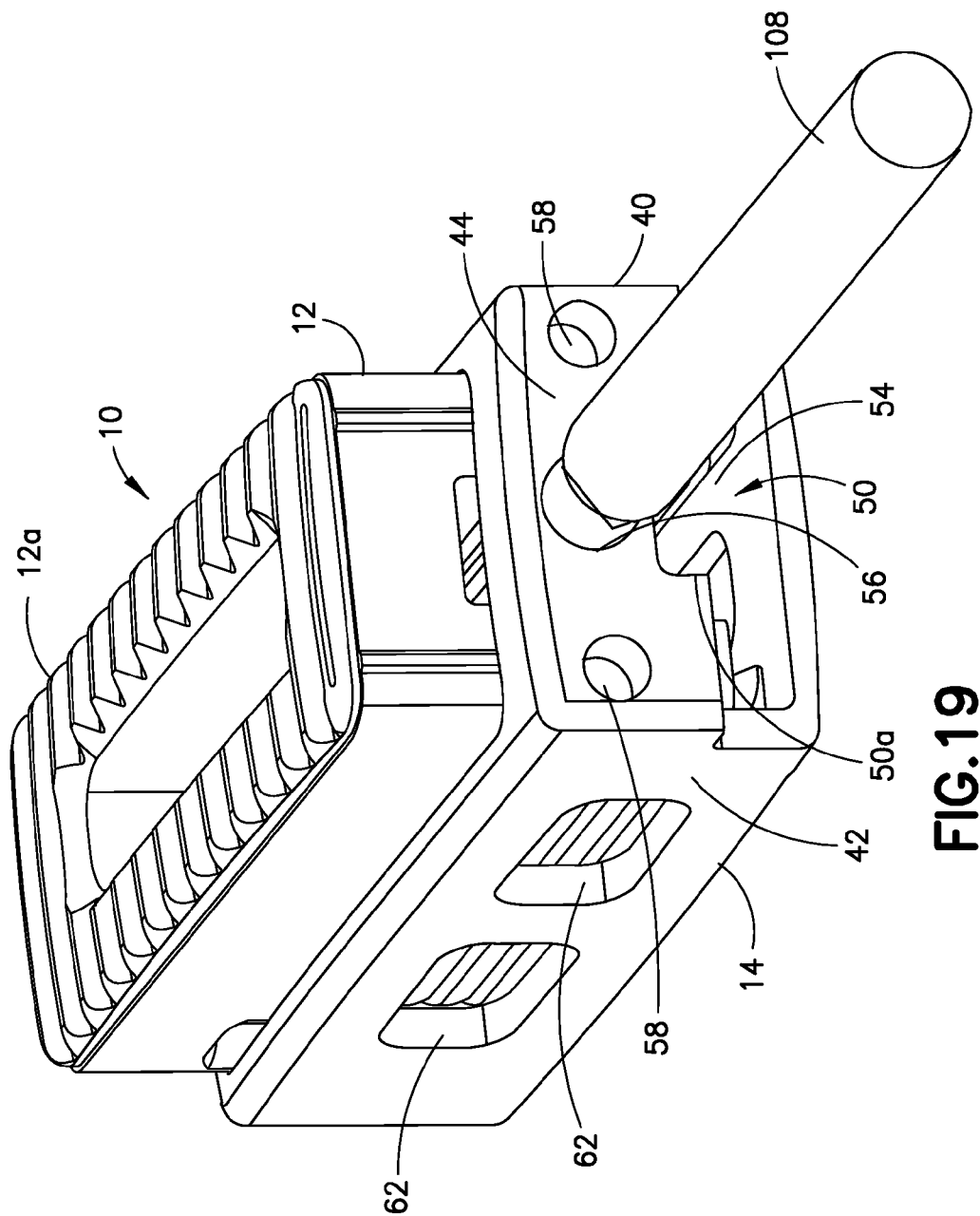
FIG. 19 is a proximal perspective view of the expanded spinal interbody fusion device with a guide pin releasably connected thereto subsequent to the inserter having been detached from the guide pin with inserts not being shown for clarity.

The inferior plate 14 as shown in FIGS. 4 and 19 includes a lower inner support surface 54 on which elevator 18 is supported. Inner surface 54 defines the bottom surface of the cavity 48. Inferior endplate 14 further defines a fully bounded insert channel 50 extending through the rear end wall 44 in communication with interior cavity 48 and through which one or more inserts 16 are introduced. The height of channel 50 as measured vertically from inner surface 54 is slightly greater than the combined thicknesses of insert 16 and elevator 18. With insert 16 being slidably received through channel 50 on top of elevator 18, as will be described, only one insert 16 may be introduced at a time. As device 10 is expanded and further inserts 16 are sequentially introduced, all inserts 16 lying above the lowermost insert 16, which would be situated on top of elevator 18, will be prevented from backing out of the device 10 by the interior surface 44*a* of rear end wall 44 (FIG. 4). The rear end wall 44 further defines a threaded connection opening 56 (FIG. 10*a*) for threaded releasable receipt of a guide pin 108 for use in the introduction of inserts 16 and in the delivery of bone graft material into the device 10, as will also be described. Rear end wall 44 may also additionally include a pair of bilateral openings, such as holes 58, adjacent the sidewalls 40 and 42 for use in releasably attaching the inserter 100 to the device 10 for the establishment of a rigid connection to the device 10 for insertion into the intradiscal space.

Figure 5A:
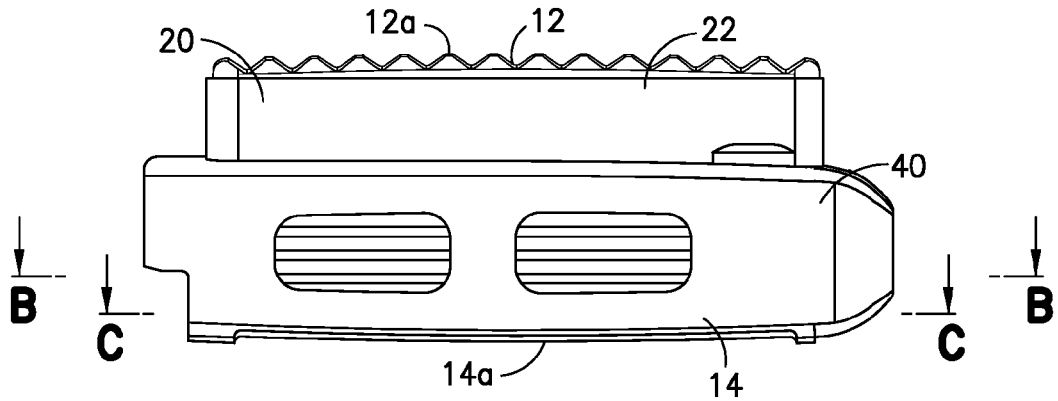
FIG. 5a is a side elevation view of the expanded device of FIG. 3b.
Figure 5B:
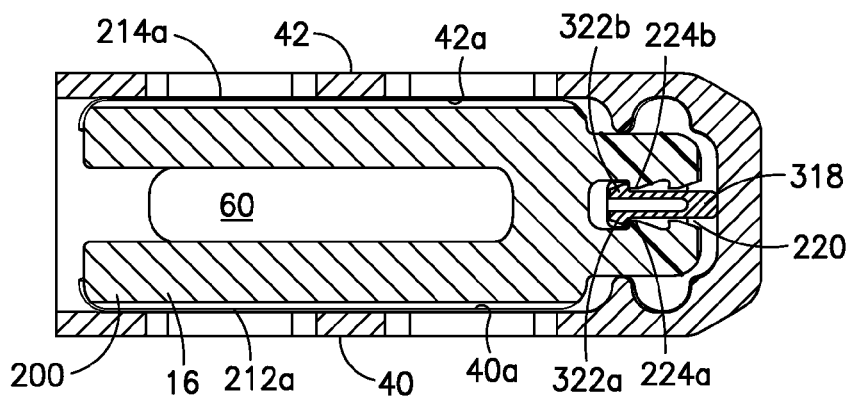
Figure 5C:
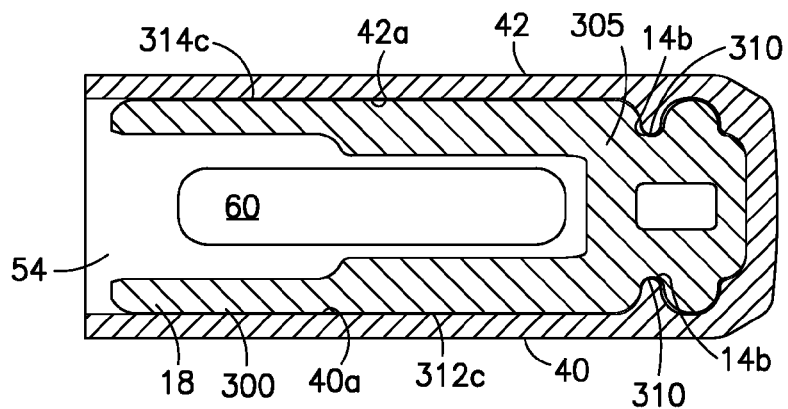
Figure 6A:
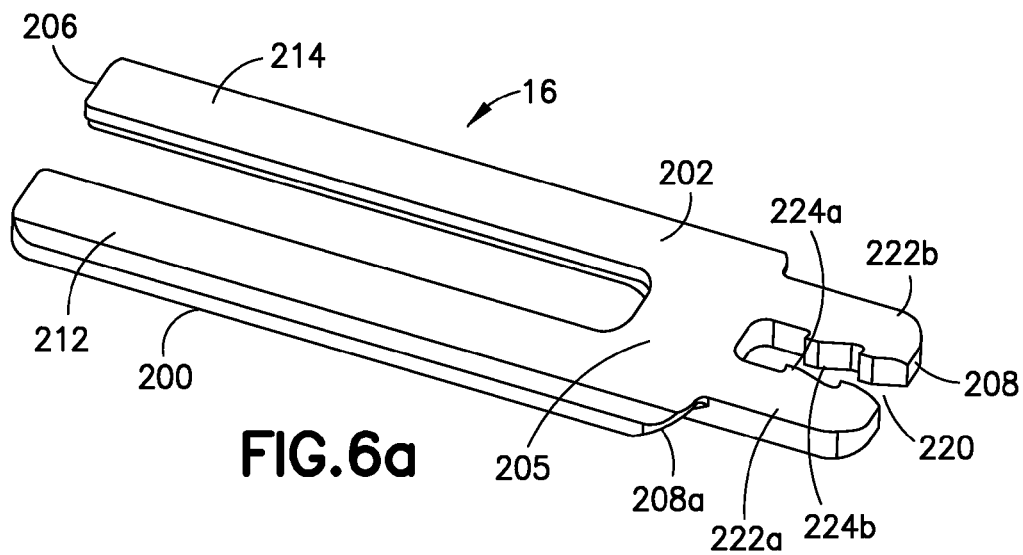
Figure 6B:
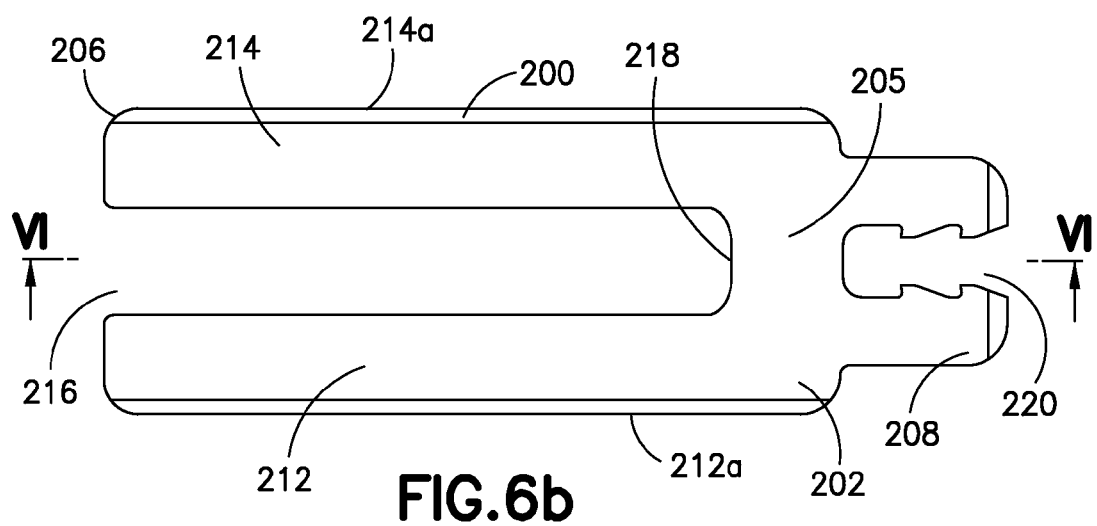
Figure 6C:
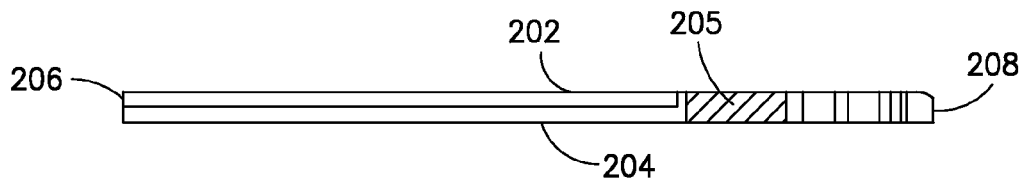
FIG. 6c is a longitudinal cross-sectional view of the insert as seen along viewing lines VI-VI of FIG. 6b.
Figure 6D:
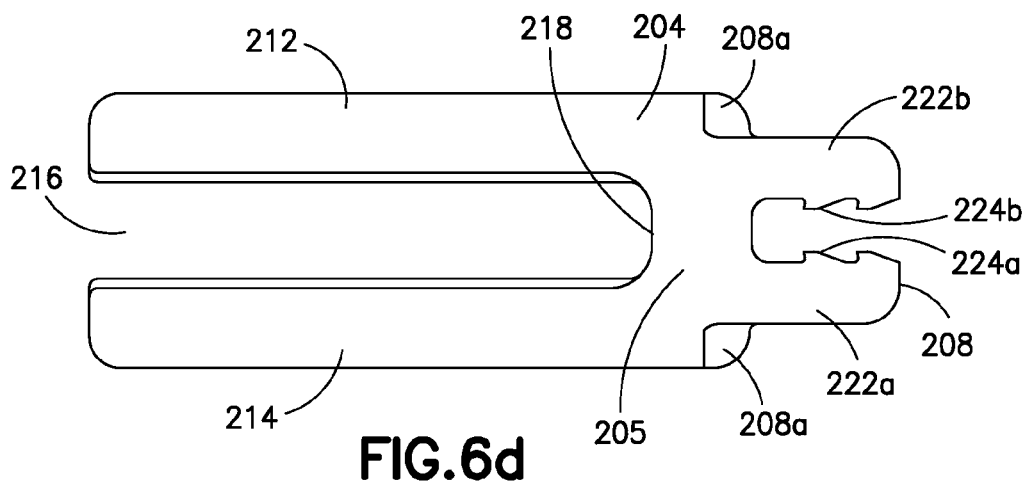
Figure 6E:
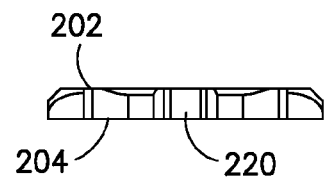
Figure 7A:
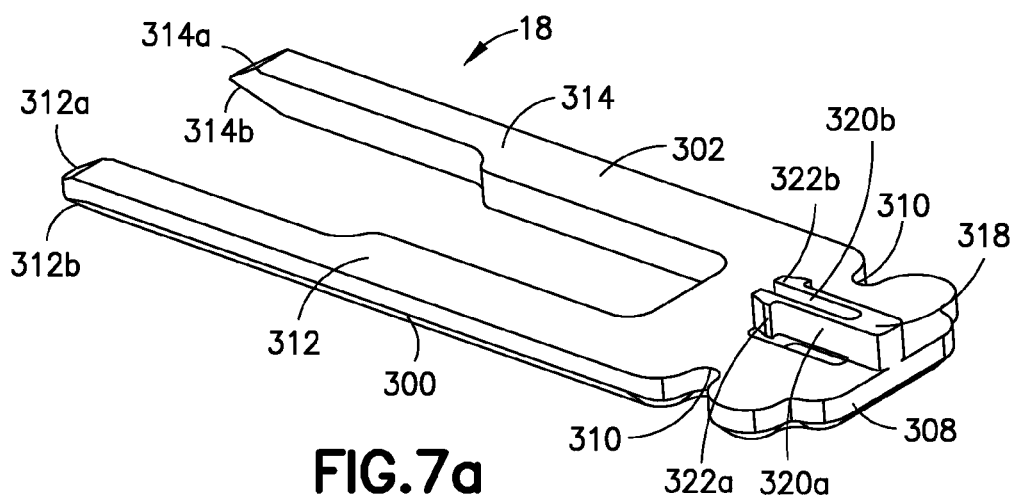
Figure 7B:
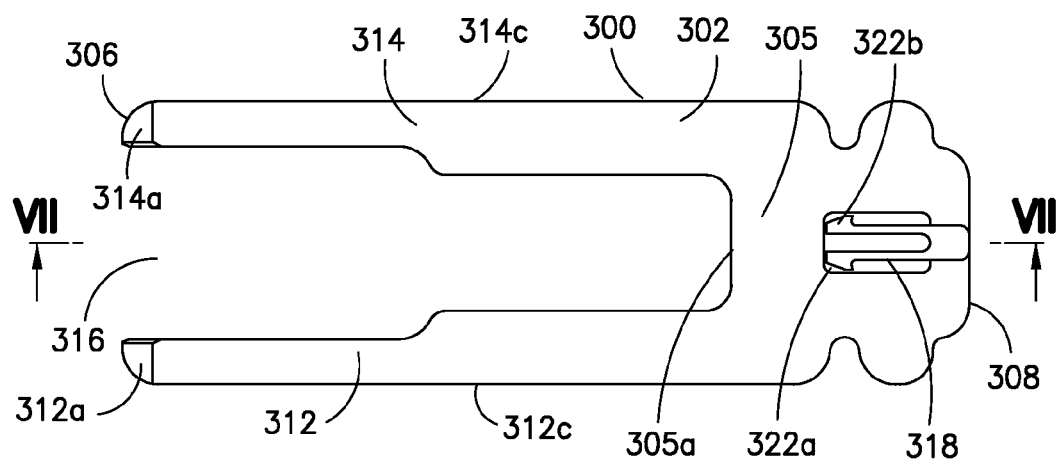
Figure 7C:
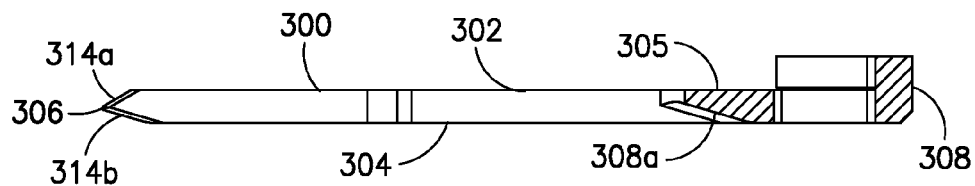
FIG. 7c is a longitudinal cross-sectional view of the elevator as seen along viewing lines VII-VII of FIG. 7b.
Figure 7D:
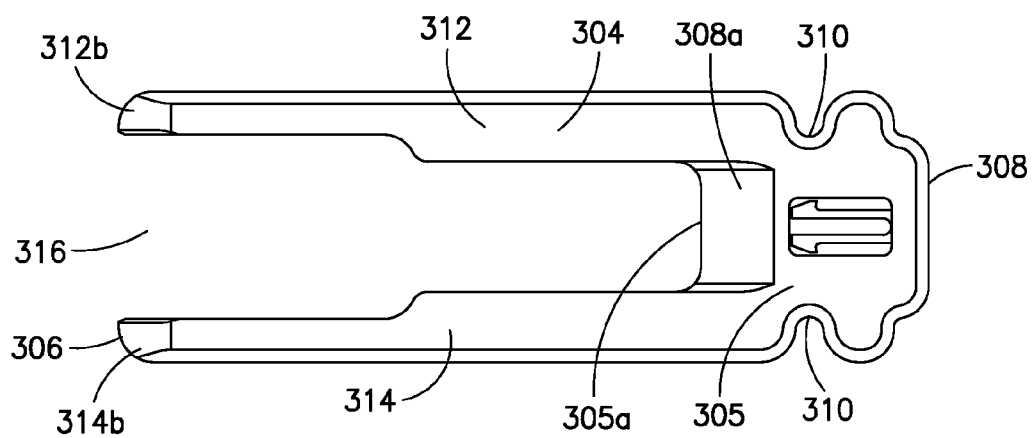
Figure 7E:
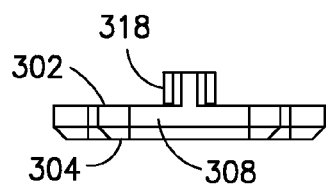

Elevator 18 is supported on inner surface 54 of inferior endplate 14 with the lateral width of elevator 18 being dimensioned for relatively close sliding fit between opposite interior surfaces 40*a* and 42*a* of side walls 40 and 42, as shown in FIGS. 5*c* and 18. As such, lateral movement of elevator 18 in directions transverse to the direction of expansion is substantially constrained. In addition, inferior endplate 14 includes a rail 14*b* projecting inwardly from each interior surface 40*a* and 42*a* and upwardly from lower inner surface 54 toward superior endplate 12. The upward projection of each rail 14*b* from inner surface 54 is slightly greater than twice the thickness of elevator 18. Rails 14*b* slidably project into recesses 310 extending into the base 305 of elevator 18 at each lateral side. Rails 14*b* substantially constrain movement of elevator 18 in the axial direction while the clearance in recesses 310 allows free movement of elevator 18 in the direction of expansion along rails 14*b* as shown by the arrow 130 in FIG. 10*a*. As such, elevator 18 is captively supported within inferior endplate 14 and is independently movable along the direction of expansion toward and away from each of the superior endplate 12 and the inferior endplate 14.

As shown particularly in FIGS. 4, 5*a-b* and 18, the inferior endplate 14 includes a graft chamber defined by an opening 60 extending through the lower outer surface 14*a* and the lower inner surface 54 in communication with cavity 48. In accordance with one arrangement, the inferior endplate 14 is formed of a material different from the material of the superior endplate 12. In this aspect, the inferior endplate 14 may be formed of a biocompatible metal, such as titanium, for its strength properties. Titanium is chosen for strength, biocompatibility, processing capability, and fluoroscopic imaging properties (radiolucency). Other alternative materials include cobalt chrome, stainless steel (both stronger than titanium but much less radiolucent), or biocompatible ceramics such as silicon nitride or zirconia, which are radiolucent. Titanium and silicon nitride have demonstrated good apposition to bone and superiority to PEEK. In this regard where inferior endplate 14 is formed of titanium, the lower outer surface 14*a* would provide for the promotion of bone growth. Lower outer surface 14*a* may also, however, be coated with a suitable layer of bone growth promotion material, such as titanium, and deposited in a conventional manner so as to match the roughness/porosity of the superior endplate outer surface 12*a*.

Where inferior endplate 14 is formed of titanium or other suitable metal that is radiopaque, windows 62 may be formed through sidewalls 40 and 42 as shown in FIGS. 3*a-b* and 19 so as to allow visual observation of bony through growth by suitable imaging techniques, such as fluoroscopy. Further details of interbody fusion device 10 are described in commonly assigned U.S. Pat. No. 8,900,312, patent application Ser. No. 13/795,054 entitled "Expandable Interbody Fusion Device with Graft Chambers", filed on Mar. 12, 2013 ("the '312 patent") and incorporated herein by reference in its entirety.

Details of insert 16 are shown in FIGS. 6*a-e*. The insert 16 comprises an elongate and generally flat body 200 having an upper surface 202 and a lower surface 204, both of which are generally planar and substantially parallel so that the inserts 16 can form a stable stack within the interbody fusion device 10 upon expansion. Insert 16 includes a trailing rear proximal end 206 and a leading front distal end 208. The body 200 is formed to have a generally U-shaped, horseshoe configuration, with a pair of spaced opposing arms 212 and 214 projecting rearwardly from a base 205 and defining a rearwardly facing generally U-shaped opening 216 extending through the rear end 206 and through upper surface 202 and lower surface 204. The lateral width of body 200 between side surfaces 212*a* and 214*a* is dimensioned for a relatively close sliding fit between interior surfaces 40*a* and 42*a* of side walls 40 and 42 of inferior endplate 14, as shown in FIG. 5*b*. Such close dimensioning reduces the potential of lateral movement of insert 16 during insert introduction and within cavity 48 of inferior endplate 14. A surface 218 between the upper surface 202 and the lower surface 204 at the base 205 of opening 216 defines a pushing surface for receipt of a driver of inserter 10, as will be described. The opening 216 at the rear end of each insert 200 is provided to allow bone graft material to flow into the device 10 through the insert openings 216 and into the openings 38 and 60 extending through the superior endplate 12 and the inferior endplate 14, respectively. A pair of inclined surfaces 208*a* extends upwardly from and communicating with lower surface 204 on each lateral side the insert 16 adjacent the front distal end 208.

The insert 16 includes a feature for interlocking engagement with elevator 18 in a complementary cooperative connection. Distal front end 208 of insert body 200 includes therein a latching receptacle 220 defined by a pair of spaced opposing arms 222a and 222b for receipt therein of a flexible latch 318 (FIG. 7a-e) on elevator 18, as will be described. Arms 222a and 222b include inwardly projecting locking surfaces 224a and 224b respectively for cooperative locking engagement with elevator latch 318. Unlike the inserts described in the '312 patent, the inserts 16 described herein do not function to assist in the separation of superior endplate 12 and inferior endplate 14 or any subsequent inserts 16 inserted into interbody fusion device 16, as that lifting function is provided herein by inserter 100 in conjunction with elevator 18. It is contemplated that the inserts 16 described herein be formed of a biocompatible material that is sufficiently rigid to form a solid stack as the successive inserts are inserted into the device. Thus, in one specific embodiment, the inserts 16 are formed of PEEK or a carbon-fiber reinforced PEEK, or similar polymeric material.

Turning now to FIGS. 7a-e, details of the elevator 18 are shown. The elevator 18 comprises an elongate and generally flat body 300 having an upper surface 302 and a lower surface 304, both of which are generally planar and substantially parallel. The elevator 18 has a thickness between upper surface 302 and lower surface 304 that is slightly greater than the thickness of insert 16. As such, when as noted below the thickness of an insert 16 is, for example, 1.0 mm, the thickness of elevator 18 may be 1.03 mm. Elevator 18 includes a trailing rear proximal end 306 and a leading front distal end 308. The elevator body 300 is formed to have a generally U-shaped, horseshoe configuration similar to the configuration of insert 16. Elevator body 300 includes a pair of spaced opposing arms 312 and 314 projecting rearwardly from a base 305 and defining a rearwardly facing generally U-shaped opening 316 extending through the rear end 306 and through upper surface 302 and lower surface 304. Base 305 has a rearwardly facing surface 305a that communicates with opening 316. The opening 316 at the rear end of elevator 18 is provided to allow bone graft material introduced into the device 10 to flow through the insert openings 216 of inserts 16 and into the openings 38 and 60 extending through the superior endplate 12 and the inferior endplate 14, respectively. The rear proximal end 306 includes an inclined surface 312a and 314a, respectively at the free end of each arm 312 and 314 extending downwardly from and communicating with the upper surface 302. The rear proximal end 306 further includes an inclined lifting surface 312b and 314b, respectively at the free end of each arm 312 and 314 extending upwardly from and communicating with the lower surface 304. The front distal end 308 includes adjacent base surface 305a an inclined lifting surface 308a extending upwardly from and communicating with lower surface 304. The inclined lifting surfaces 312b, 314b and 308a are angled in the same direction with approximately equal angles. The lifting surfaces 312b, 314b and 308a define inclined ramps with multiple points of contact for cooperative contact with complementary surfaces of an expansion component on the inserter 100 for lifting elevator 18, as will be described. Inclined surface 308a is generally centrally located along the elongate axis of elevator, while surfaces 312b and 314b are spaced bilaterally. Thus, lifting surfaces 308a, 312b and 314b define three triangulated points of contact. Elevator has a recess 310 extending into the elevator base 305 at each lateral side thereof. Recesses 310 are sized to receive rails 14b on the interior surfaces of inferior endplate 14, as described. In one specific embodiment, the elevator 18 is formed of titanium alloy, type 2, which may be anodized for lubricity. Other materials, such as PEEK, may also be used as the material for elevator 18.

Distal front end of elevator body 300 includes a flexible latch 318 projecting upwardly from upper surface 302. Latch 318 comprises a pair of spaced opposing flexible arms 320a and 320b that are configured to flex toward each other. Flexible arms 320a and 320b include outwardly directed locking surfaces 322a and 322b respectively, for cooperative receipt within receptacle 220 of each insert 16, as shown in FIG. 5b. Upon receipt of latch 318 into receptacle 220, locking surfaces 224a and 224b resiliently engage locking surfaces 322a and 322b, respectively. Latch 318 projects above the upper surface 302 and a height slightly greater than the thickness of an insert 16. The lateral width of elevator body 300 between the side surfaces 312c and 314c, respectively of arms 312 and 314 is dimensioned for a relatively close sliding fit as noted hereinabove between interior surfaces 40a and 42a of inferior endplate 14, as shown in FIG. 5c.

Turning again now to FIGS. 1a-c and FIGS. 8 and 8a, details of the inserter 100 are described. Inserter 100 is elongate having a distal end 100a and at a proximal end 100b a frame 101. A trigger actuator 102 to effect expansion of device 10 and insertion of inserts 16 into device 10 after expansion includes a frame 101 at the proximal end 100b of inserter. A plurality of inserts 16 are movably supported in a linear array on an elongate track 104 for individual successive insertion into device 10. Track 104 supports at least one insert 16 and may, for example, support an array of five inserts 16, although fewer or more inserts 16 may be supported as desired.

Figure 8A:
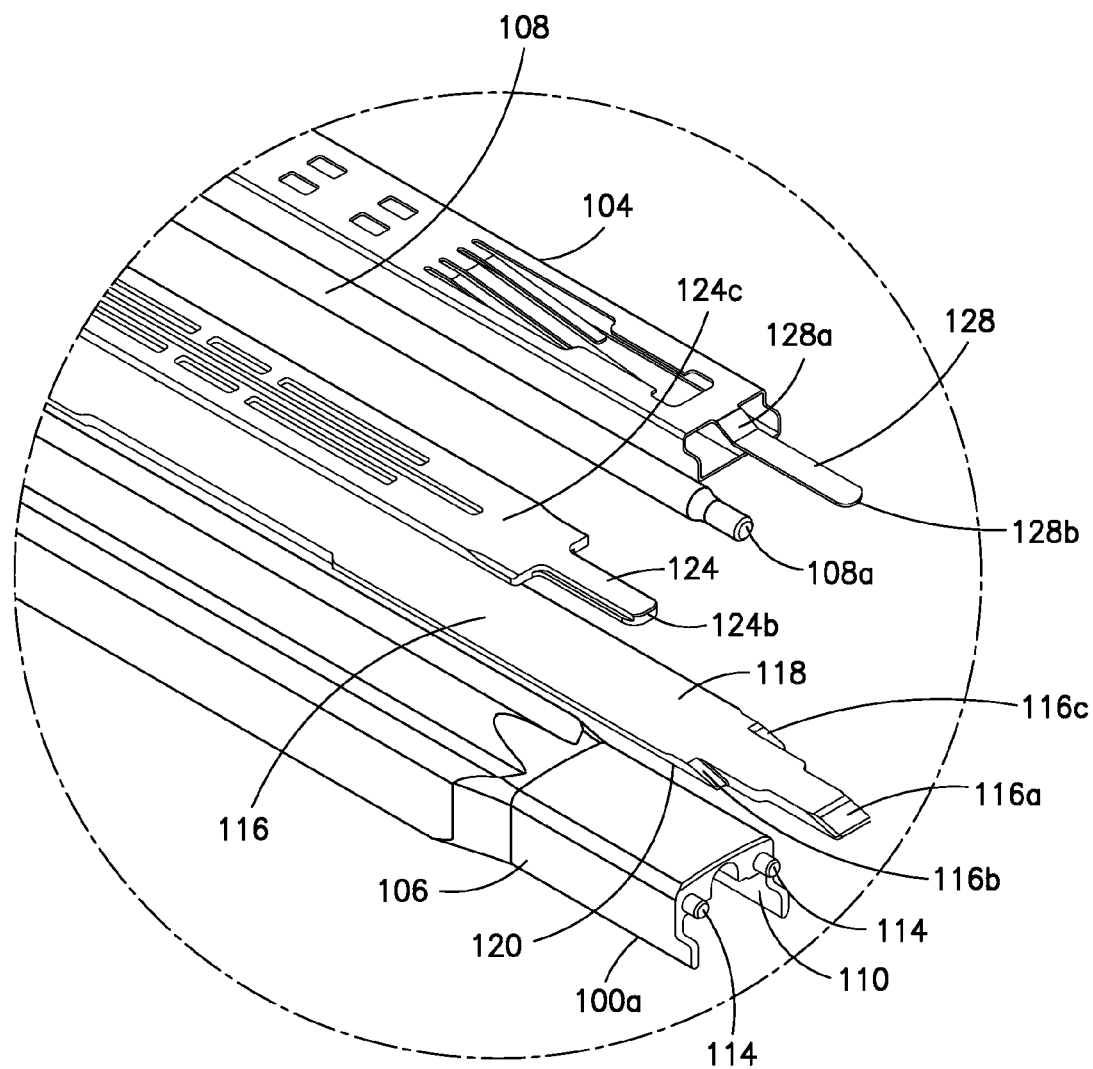
FIG. 8a is an enlarged view of the distal portion of the inserter track and components as circled in FIG. 8.

The distal end 100a is shown in exploded detail in FIGS. 8 and 8a. The inserter 100 includes elongate track 104 and an outer elongate track cover 106, the cover 106 being substantially rigidly joined to track 104. Track 104 is configured as a closed channel and is supported within outer track cover 106. Cover 106 is fixedly secured to frame 101, although in a particular arrangement as will be described, cover 106 may be removably attached to frame 101. An elongate guide pin 108 is supported within an opening 110 extending lengthwise through the cover 106. The distal end 108a of the guide pin 108 is threaded for releasable threaded engagement into opening 56 in the proximal rear end wall 44 of the inferior endplate 14. The proximal end of guide pin 108 is provided with a threaded knob 112 for compressing and releasably attaching the cover 106, and thereby the track 104 to the device 10. The track cover 106, in one arrangement, includes a pair of opposing pins 114 that engage corresponding holes 58 in rear wall 44 of inferior endplate 14 (FIG. 19) to assist in rigidly securing the inserter 100 to the device 10. It should be appreciated that other securement structure may be used to releasably attach the inserter 100 to the device 10. Track 104, in one embodiment, is formed of stamped stainless steel and cover 106 is an extruded aluminum alloy. Stainless steel or strong reinforced plastic could also be used for cover 106.

The track 104 at the distal end 100a of the inserter 100 supports an expansion component defined by an axially translatable lifting platform 116 movably supported on track 104 for relative axial movement thereto to cooperatively slidably contact elevator 18 for expanding the device 10. The lifting platform 116 is elongate and generally flat having an upper surface 118 and a lower surface 120, both of which are generally planar and substantially parallel (FIG. 18). The lifting platform 116 has a thickness between upper surface 118 and lower surface 120 that is dimensioned to be the same as the thickness of elevator 18, i.e., slightly greater than the thickness of an insert 16. Lifting platform 116 is supported by the inserter 100 for reciprocating axial movement in projecting and retracting directions. The proximal end of the lifting platform 116d is coupled to the trigger actuator 102 to effect such projecting and retracting directions, as will be described.

Lifting platform 116 projects slidably axially outwardly from track 104 and includes at its free distal end an inclined lifting surface 116a extending downwardly from and communicating with upper surface 118. At a location spaced proximally of lifting surface 116a, lifting platform further includes a pair of laterally spaced inclined surfaces 116b and 116c. The inclined lifting surfaces 116a, 116b and 116c are angled in the same direction with angles approximately equal to the angles respectively of inclined lifting surfaces 312b, 314b and 308a of elevator body 300. Inclined surfaces 116a, 116b and 116c define inclined ramps with multiple complementary points of contact for cooperative contact with elevator 18. Inclined surface 116a is generally centrally located along the elongate axis of lifting platform 116, while surfaces 116b and 116c are spaced bilaterally. Thus, lifting surfaces 116a, 116b and 116c define three triangulated points of contact that are located and spaced to cooperatively contact lifting surfaces 308a, 312b, and 314b, respectively during movement of lifting platform 116 in the projecting direction. Lifting platform 116, particularly inclined surfaces 116a, 116b and 116c, may be coated or otherwise include a suitable lubricant to facilitate sliding contact with elevator 18 for expansion of device 10. Where lifting platform 116 is made of stainless steel, for example, such lubricant may include a molybdenum disulfide ($MoS_2$) material.

Still referring to FIGS. 8 and 8a, inserter 100 further supports at its distal end 100a a driver 124 for axial translational movement within track 104. The proximal end 124a (FIG. 8) of driver 124 is coupled to trigger actuator 102 to effect translational movement of the driver 124, as will be described. The distal end of driver 124 comprises a pushing surface 124b sized and configured to enter into the opening 216 of an insert body 200 to engage pushing surface 218 and push the insert 16 from track 104 into the device 10 upon axial distal movement of driver 124. Furthermore, driver 124 includes an upper surface 124c on which inserts 16 are movably supported in a linear array. Also included as shown in FIG. 8 is an indexing member 125 that cooperates with driver 124 to distally incrementally move inserts 16 in the projecting direction to be positioned for individual contact with driver pushing surface 124b while preventing retrograde movement of inserts 16 as they are positioned.

With further reference still to FIG. 8a, inserter 100 comprises a flexible graft shield 128 projecting distally from inner track 104. Graft shield 128 is supported at one end 128a in a cantilevered manner with an opposite end 128b being unsupported and free to flex. Graft shield 128 is elongate and generally flat and is sized and configured to substantially block communication between the opening 38 through the superior endplate 12 and inserts 16 slidably inserted into device 10. As will be described, graft shield 128 is configured to extend into device 10 through channel 50 between the superior endplate 12 and the expansion structure adjacent the lower surface 30 of the superior endplate 12.

Figure 9:
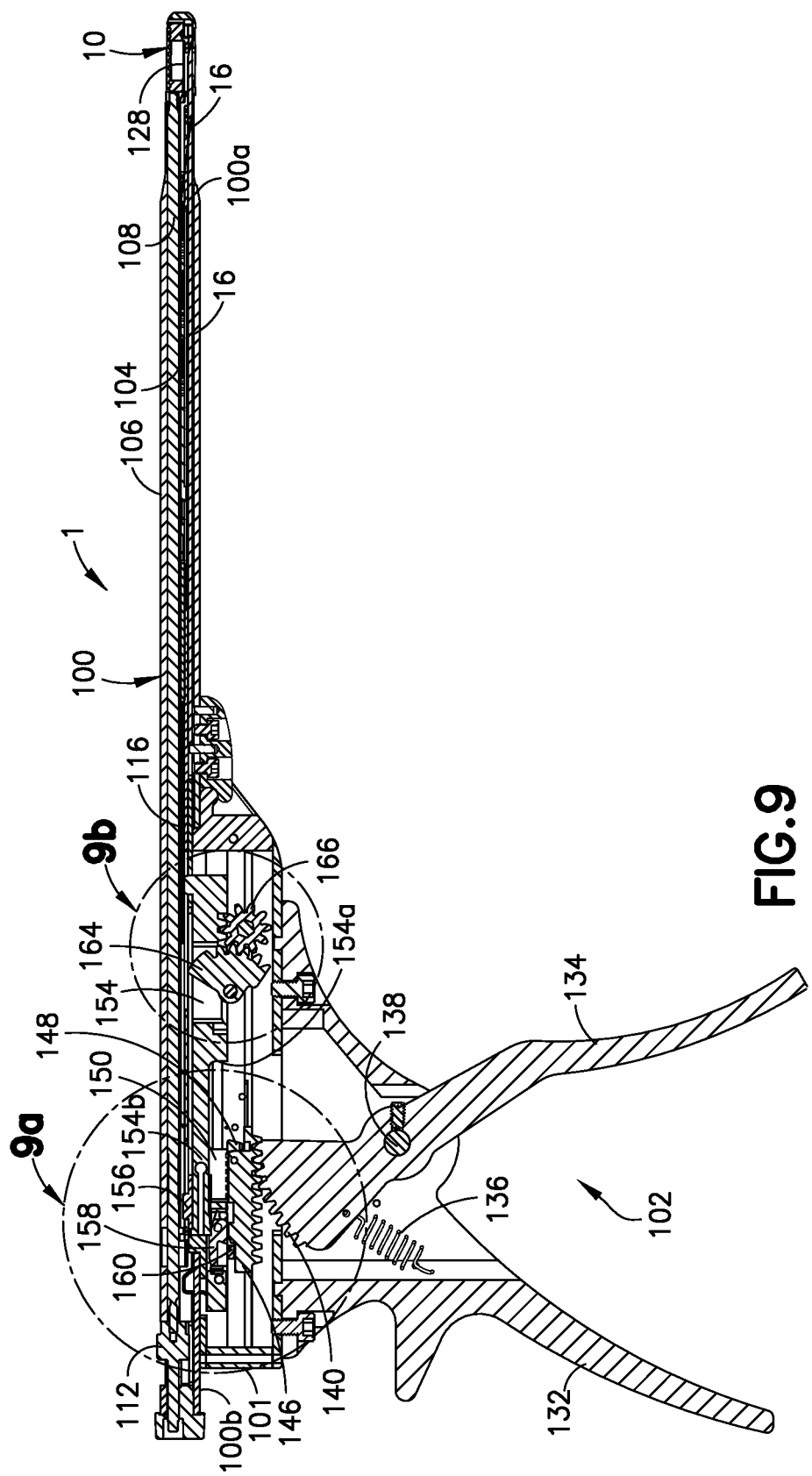
FIG. 9 is a cross-sectional view of the inserter and device of FIG. 1a as seen along viewing lines IX-IX of FIG. 1c.

Turning now to FIGS. 9 and 9a-b, the details of the trigger actuator 102 of the inserter 100 and its operating mechanism and function are described. Trigger actuator 102 comprises a pair of hand grips 132 and 134 biased apart by an extension spring 136. Hand grip 132 is fixedly secured to frame 101 of inserter 100. Hand grip 134 is pivotally connected to frame 101 at pivot point 138 and is movable toward hand grip 132 against the bias of extension spring 136 by manual pressure. Hand grip 134 has gear teeth 140 that interface with a gear rack 146 slidably coupled to the frame 101. The gear mechanism is sized to provide the appropriate translation of the gear rack 146 in the projecting direction as trigger actuator 102 is actuated. Also slidably coupled to the frame 101 are a driving slide 150 that is configured for relative and joint movement with driver 124, and a lifting slide 154 that is configured for joint movement with lifting platform 116. Gear rack 146 includes a lower surface 146a defining a tooth pattern, an upper surface 146b defining a pushing surface 146d, a ramp surface 146e, and a distal end 146c. Distal end 146c includes a pawl 148 configured for limited rotation about pivot point 148a, the distal end of pawl 148 being biased toward the driving slide 150 by a compression spring 152. Prior to actuation of trigger 102 the pawl 148 is constrained from rotation about pivot point 148a by the lower surface 150a of driving slide 150. Upon a first actuation of trigger 102, and therefor translation of the gear rack 146 in the projecting direction, the pawl 148, under bias of compression spring 152, slides along lower surface 150a. When sufficient translation of gear rack 146 has occurred such that the pawl 148 has passed the distal end of driving slide 150, pawl 148 rotates counterclockwise as viewed in FIG. 9a about pivot point 148a to a position limited by contact with upper surface 146f of gear rack 146.

Pawl 148 includes a pushing surface 148b sized to engage pushing surface 154a at proximal end of lifting slide 154. Further actuation of the trigger 102 promotes contact of pushing surfaces 148b and 154a and therefor movement of the lifting slide 154 and lifting platform 116 in the projecting direction causing expansion of the device 10.

Lifting slide 154 further includes a proximal elongate tethering portion 154b with pushing surface 154c sized to engage pushing surface 150b at proximal end of driving slide 150. Upon translation of lifting slide 154 in the projecting direction, pushing surface 154c engages pushing surface 150b for joint translation therebetween.

Driving slide 150 further includes an upper boss feature 156 defining pushing surfaces 156a and 156b sized to fit within slot a 124d (FIG. 8) of driver 124. Slot 124d comprises complementary axially spaced apart pushing surfaces 124e and 124f, respectively. The length of slot 124d is sized such that translation of driving slide 150 during first actuation of trigger 102 does not induce contact between pushing surfaces 156b and 124f and therefore does not impart translation of driver 124.

Driving slide 150 further includes a pawl 158 configured for limited rotation about pivot point 158a, the proximal end of pawl being biased toward the gear rack 146 by bilateral torsion springs (not shown). Prior to actuation of trigger 102 the pawl 148 is constrained from rotation about pivot point 158a by a ledge surface 160 rigidly coupled to frame 101. Upon translation of the driving slide 150 in the projecting direction, the pawl 158, under bias of the torsion springs, slides along upper ledge surface 160. When sufficient translation of driving slide 150 has occurred such that the pawl 158 has passed the distal end of ledge surface 160, pawl 158 rotates counterclockwise as viewed in FIG. 9a about pivot point 158a to a position limited by contact with lower surface 150c of driving slide 150. Such translation is configured to be slightly longer than the translation required by the lifting platform 116 to achieve full expansion of device 10 such that rotation of pawl 158 will not occur in the absence of full expansion of device 10. Further, rigidly coupled to pawl 158 for rotation therewith are bilateral flags 162 positioned in slots 163 in frame 101 (FIG. 1a), the flags 162 projecting laterally outwardly of both sides of frame 101. Upon joint rotation of pawl 158 and flags 162 the user is visually alerted to the position of the driving slide 150 and lifting slide 154 thereby indicating to the user that full expansion of device 10 has been achieved and that no further inserts can be introduced.

Pawl 158 further comprises a pushing surface 158b sized to engage pushing surface 146d of gear rack 146 and a ramp surface 158c sized to engage ramp surface 146e of gear rack 146. After full actuation and a complete stroke of trigger 102 and release of grip pressure, the gear rack 146 and hand grips 132/134 are returned under the bias of the extension spring 136. During retraction of the gear rack 146, cooperative ramp surfaces 146e and 158c collide inducing pawl 158 to rotate clockwise thereby allowing passage of the gear rack 146. Upon sufficient translation of the gear rack 146 in the retracting direction such that the ramp surface 146e has passed the proximal edge of ramp 158c, pawl 158 rotates counterclockwise about pivot point 158a back to a position limited by contact with lower surface 150c of driving slide 150.

It should be appreciated that upon completion of first actuation of trigger 102 and completion of the first stroke, lifting platform 116 remains projected maintaining the expanded state of device 10 and that driving slide 150 remains in a partially projected state due to tether 154b of lifting slide 154. It should also be noted that pawl 158 remains in a rotated state limited by contact with driving slide 150 while pawl 148 is returned to its original collapsed state limited by lower surface 150a of driving slide 150.

Upon a second actuation of trigger 102 gear rack 146 translates again in the projecting direction such that pushing surface 146d contacts pushing surface 158b of pawl 158 causing joint translation of gear rack 146 and driving slide 150. Upon further actuation, pushing surface 156b of driving slide 150 contacts pushing surface 124f of driver 124 causing joint translation therebetween, thereby engaging pushing surface 218 of insert 16 and pushing the insert 16 from track 104 into the device 10 during completion of the second stroke of trigger actuator 102.

For the purpose of returning the track lifting platform 116 to its original position in the retracting direction a cam 164 and gear 166 are provided. The gear 166 interfaces with a second gear rack 154d rigidly connected to the lower surface of lifting slide 154. The cam 164 is coupled to gear 166 for opposite rotation therebetween and is positioned to contact a notch 170 (FIG. 8a) in the driver 124 after an insert 16 has been partially inserted into the device 10. Further trigger actuation returns the lifting platform 116 to its original position while the driver further inserts the insert 16. When full trigger actuation is achieved, the gear rack 146 and hand grips 132/134 are returned under the bias of the extension spring 136. To reset the position of driving slide 150 manually, the user pulls up on bilateral tabs 162b rigidly coupled to flags 162 thereby imparting rotation of pawl 158 and translation of driving slide 150 in the retracting direction. Due to the rotated state of flags 162 and pawl 158, driver slide 150 can be returned to its original retracted position with pawl 158 rotation limited by ledge 160 surface. A two way ratchet mechanism 168 prevents unwanted motion of driving slide 150 in the wrong direction. In the event full expansion of device 10 is achieved and the surgeon prefers to abort the procedure without further introduction of an insert 16, hex fitting 174 (FIG. 1a) coupled to gear 166 may be actuated by a hex wrench or other suitable tool. Rotation of fitting 174 rotates gear 166 which directly translates lifting slide 154 and hence lifting platform 116 proximally to release the expansion of device 10 with no insert 16 introduced.

It should now be understood how the trigger actuator 102 operates to expand device 10 and introduce one or more inserts 16. During the first stroke, only lifting platform 116 is translated in the projecting direction to cause expansion of device 10. Driver 124 remains stationary during the entire first stroke. After the hand grips 132/134 are returned to the starting position under the bias of extension spring 136 upon completion of the first stroke, lifting platform 116 remains stationary in the projecting position maintaining the expanded state of device 10 as hand grips 132/134 return. During the second stroke of trigger actuator 102, driver 124 is translated in the projecting direction while the lifting platform 116 is initially stationary in the projecting direction. When driver 124 has inserted an insert 16 partially into the expanded device 10 continued operation of trigger actuator 102 retracts lifting platform 116 in the retracting direction. As lifting platform 116 retracts, driver 124 continues to advance in the projecting direction to push insert 16 fully into position upon completion of the second stroke.

Thus, for the particular device being described for insertion into the intradiscal space in the posterior approach, expansion of device 10 is achieved during the first stroke of trigger actuator 102 and full insertion of an insert 16 during completion the second stroke. For longer devices, such as those insertable from the lateral approach, the mechanism of inserter 100 may be adjusted such that the longer device is expanded in a first stroke, the inserts 16 inserted partially into the expanded device during a second stroke, and fully inserted in the third stroke. It should thus be appreciated by those skilled in the art that the number of strokes employed for expansion of device 10 and insertion of an insert 16 into the expanded device 10 may be varied by suitable adjustment of the operating mechanism of trigger actuator 102. Such adjustment may include, for example, varying the number of pushing surfaces 146d that are provided on gear rack 146 for engagement with pawl 158.

Turning now to FIGS. 10a-b and 11-12 the assembly of the device 10 and the inserter 100 is described. The superior endplate 12 and the inferior endplate 14 are assembled in an unexpanded condition to the inserter 100 with the superior endplate 12 residing fully within cavity 48 of inferior endplate 14. In such condition elevator 18 is captively retained between superior endplate 12 and inferior endplate 14 as described above and shown in FIG. 5c for independent movement along the direction of expansion 130. The inserter 100 is releasably attached to the device 10 upon threaded engagement of the guide pin 108 into threaded opening 56 in the proximal rear end wall 44 of the inferior endplate 14. Graft shield 128 extends into device 10 through channel 50 between the superior endplate 12 and the elevator 18 adjacent the lower surface 30 of the superior endplate 12. With the inserter 100 fixed to the device 10, lifting platform 116 and driver 124 are axially translatable relative to the device 10 in the projecting and retracting directions. In this unexpanded condition, there are no inserts 16 in the device 10. In the arrangement being described, there are five inserts 16 supported in a linear array on track 104.

Figure 10A:
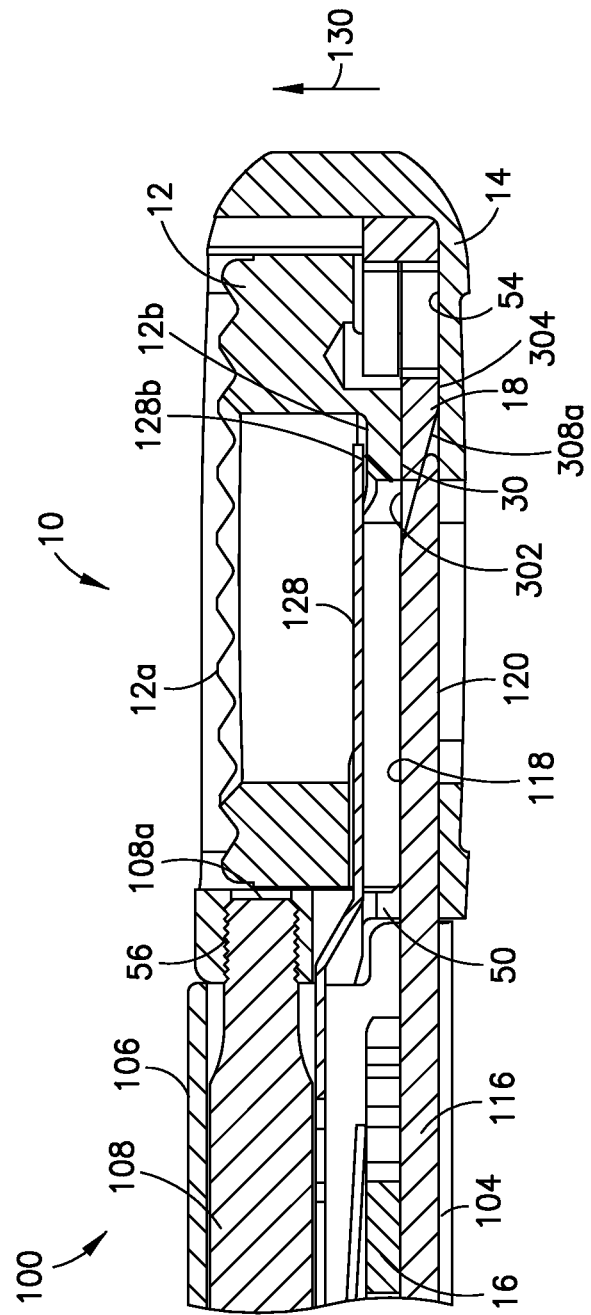
FIG. 10a is a cross-sectional view of the distal end of the inserter and device as seen along viewing lines A-A of FIG. 2 with the expandable device unexpanded.

In the position illustrated in FIGS. 10a-b and 11-12 lifting platform 116 is in a retracted position relative to device 10 and elevator 18. Insert 16, as seen in FIG. 10a, is disposed on track 104 exteriorly of and ready for insertion into device 10. In this position the lower surface 120 of lifting platform 116 is situated on lower inner surface 54 of inferior endplate 14. Likewise lower surface 304 of elevator 18 is supported by lower inner surface 54 of inferior endplate 14. As such, lifting platform 116 and elevator 18 are on substantially the same plane, with the upper surface 118 of lifting platform 116 being substantially coplanar with the upper surface 302 of elevator 18. With the inserter 100 attached to the device 10, elevator 18 is fixed in the axial direction relative to axial movement of lifting platform 116.

Figure 10B:
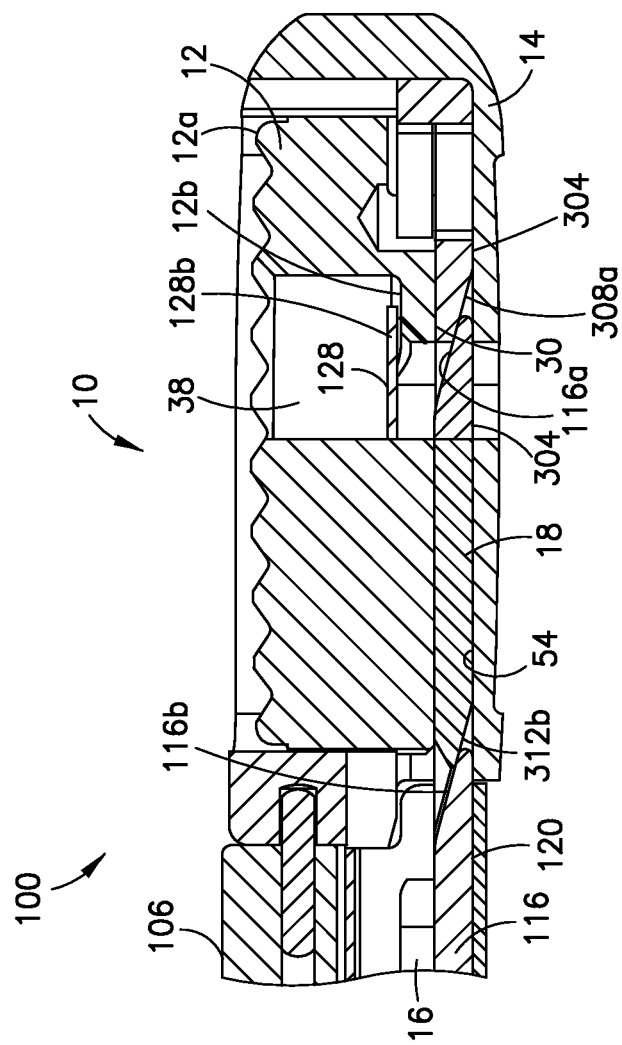
FIG. 10b is a cross-sectional view of the distal end of the inserter and device as seen along viewing lines B-B of FIG. 2 with the expandable device unexpanded.
Figure 11:
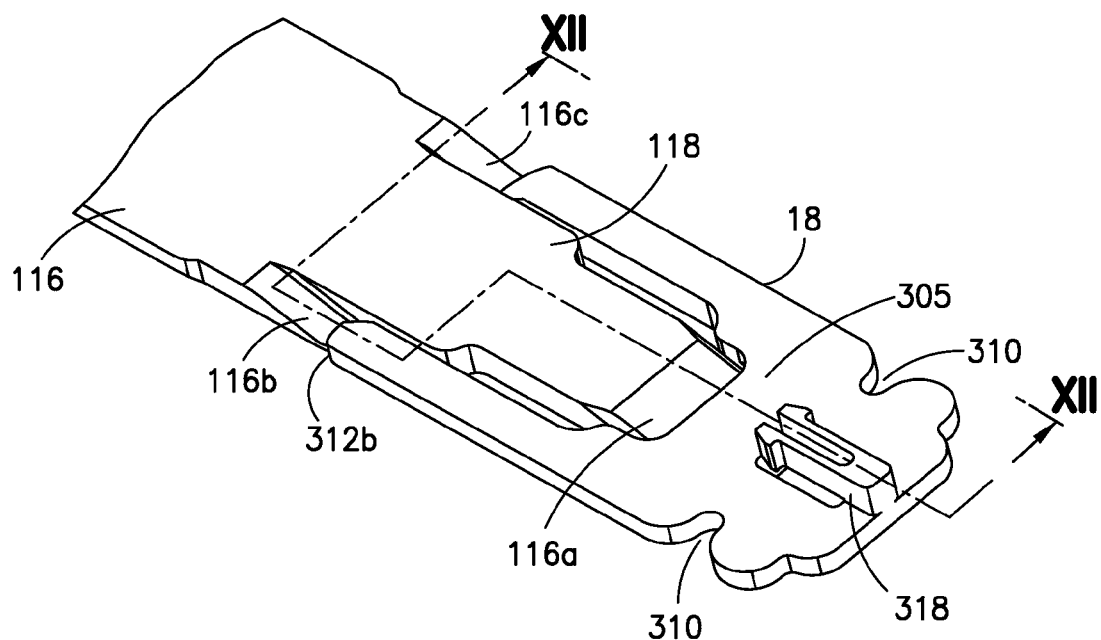
FIG. 11 is a top partial perspective view of the distal end of the lifting platform and the elevator of the expandable device in the position depicted in FIGS. 10a and 10b.
Figure 12:
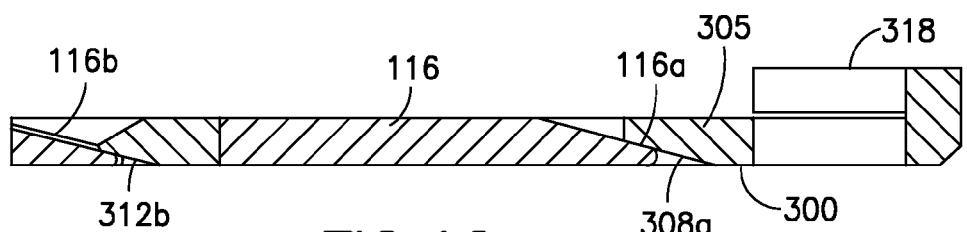
FIG. 12 is a cross-sectional view of the lifting platform and elevator as seen along viewing lines XII-XII of FIG. 11.

In the condition shown in FIGS. 10a-b, apparatus 1 comprising unexpanded device 10 releasably attached to inserter 100 is ready for use in inserting device 10 into an intradiscal space between two opposing vertebral bodies. Prior to insertion, opening 38 through superior endplate 12 may be pre-packed with a suitable bone graft material for the promotion of fusion through device 10 to the opposing vertebral bodies. Graft shield 128 extends into device 10 through channel 50 between the superior endplate 12 and the elevator 18 adjacent the lower surface 30 of the superior endplate 12 defining a pocket for receipt of the graft material. The free end 128b of graft shield 128 rests unattached on an interior ledge 12b of superior endplate 12 adjacent the distal end thereof. Opening 38 is therefore open adjacent outer surface 12a of superior endplate 12 and closed by graft shield 128 adjacent lower surface 30. As such, graft shield 128 provides a barrier between the graft material and the elevator 18 and inserts 16 inserted into device 10 during expansion. Pre-packing of bone graft material in opening 38 on graft shield 128 advantageously allows for less introduction of graft material in situ and provides more assurance that sufficient graft material will be contained throughout device 10 and into openings 38 and 60 through superior endplate 12 and inferior endplates 14 and in a stress-loaded condition against opposing vertebral bodies. In addition, graft shield 128 provides a barrier substantially preventing graft material within opening 38 from being disturbed during expansion and by substantially blocking graft material from interfering with the expansion of device 10 or with the slidable insertion of inserts 16 which may be impeded by graft material on the sliding interfacing surfaces.

Figure 13A:
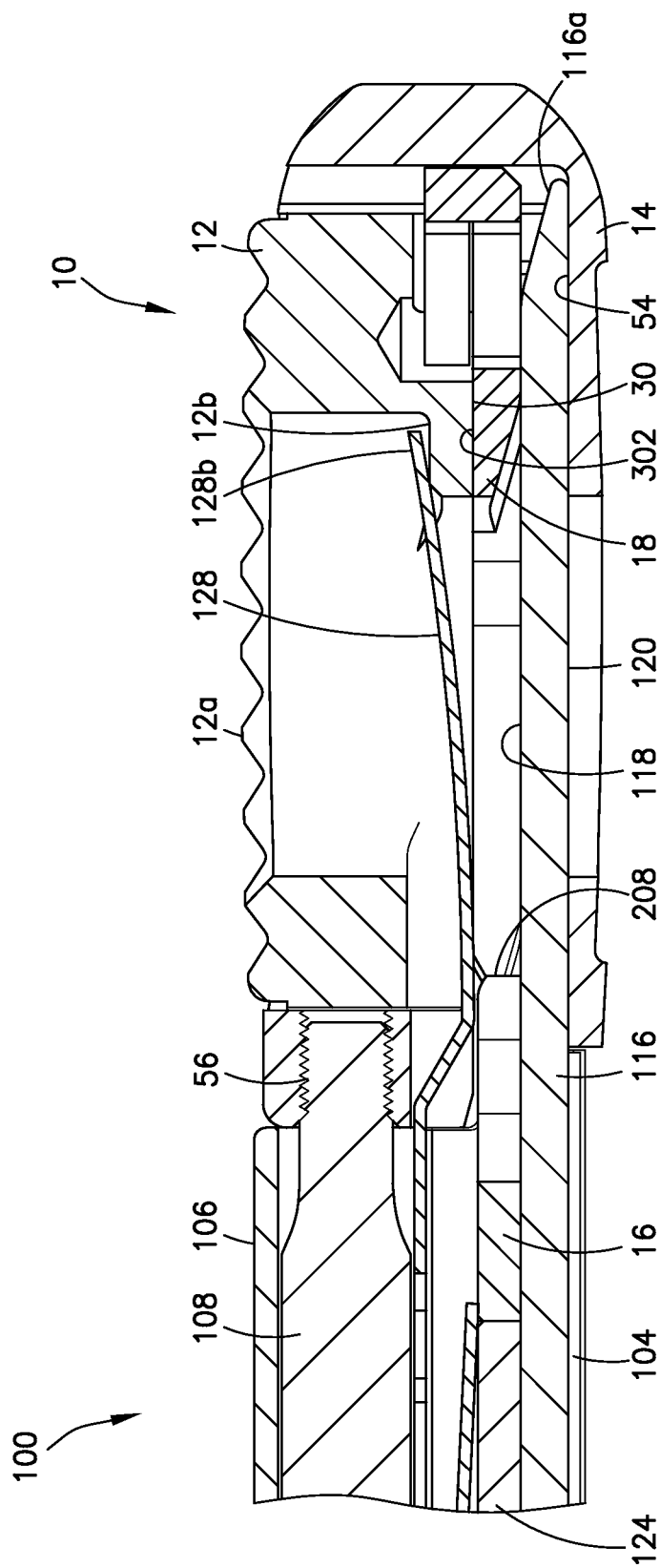
FIGS. 13a and 13b are views similar to FIGS. 10a and 10b with the lifting platform having been distally moved to a position lifting the elevator and expanding the expandable device and a first insert partially entering the expanded device.
Figure 13B:
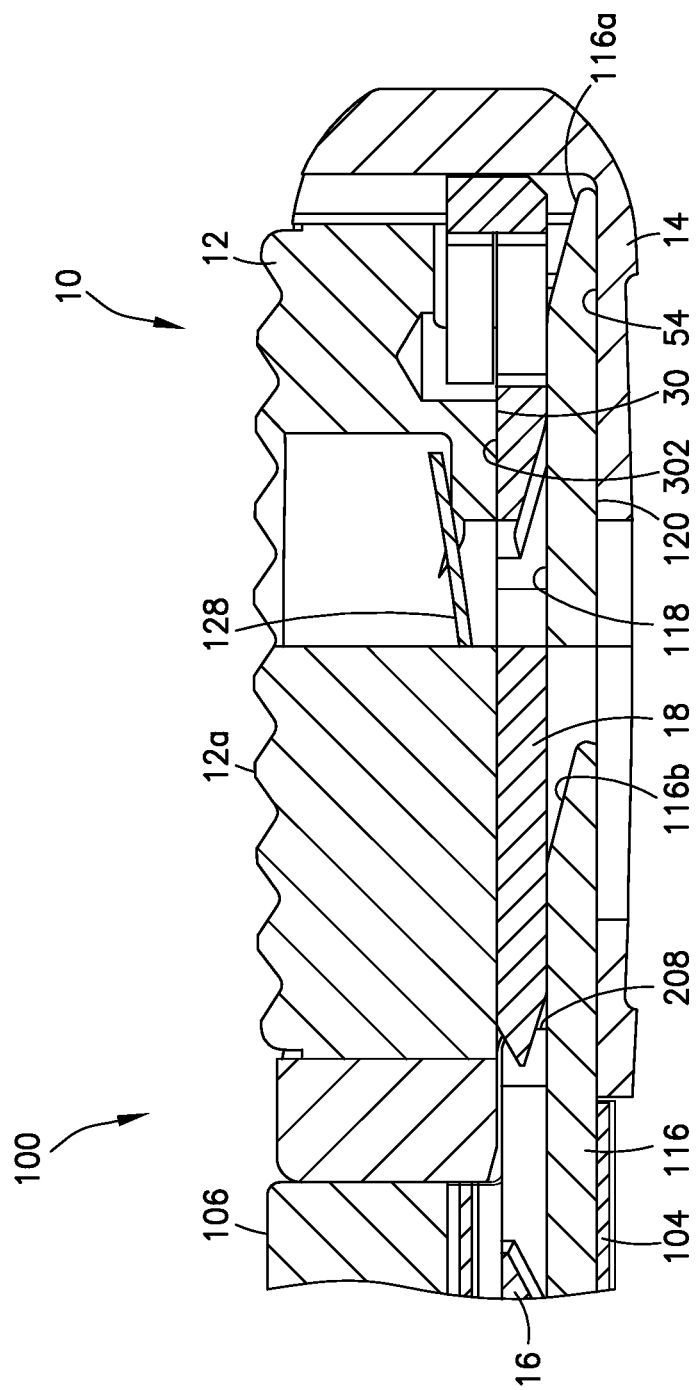

At this point in the surgical procedure, inserter 100 is used to insert unexpanded device 10 into the intradiscal space. Device 10 may be implanted as explained hereinabove into the spine posteriorly or posteriolaterally, either bilaterally or unilaterally, or in an anterior or lateral approach depending upon the surgical indication and the surgeons preference. Once device 10 is inserted in the intradiscal space in a suitable location, actuator 102 as described hereinabove is then operated in a first actuation. Initially during the first stroke lifting platform 116 is translated axially while driver 124 remains stationary. Lifting platform 116 is moved from the retracted position of FIGS. 10a-b to a projecting direction whereby lifting platform 116 is moved further into device 10. During movement in the projecting direction, lifting surfaces 116a, 116b and 116c of lifting platform 116 contact cooperative lifting surfaces 308a, 312b, and 314b, respectively of elevator 18. The cooperative engagement causes elevator 18 to move in the direction of expansion away from lower inner surface 54 of inferior endplate 14 and toward superior endplate 12. The upper surface 302 of elevator 18 contacts lower surface 30 of superior endplate 12 and elevator 18 slidably moves in the direction of expansion along rails 14b toward superior endplate 12 and away from inferior endplate 14 as shown in FIGS. 13a-b, thereby expanding device 10.

When complete expansion of device 10 is achieved the first stroke of trigger actuator 102 is completed and hand grips 132/134 are returned to the original starting position, as described above. Trigger actuator 102 is then operated in a second actuation to start a second stroke. As the second stroke commences, lifting platform 116 remains stationary holding device 10 in the expanded condition while axial translation of driver 124 begins. Continued operation of actuator 102 pushes insert 16 distally so that the distal front end 208 moves freely into expanded device 10 through channel 50 until the distal front end 208 of insert 16 is partially inserted into expanded device 10 between superior endplate 12 and inferior endplate 14 adjacent the proximal end of device 10, as illustrated in FIGS. 13a-b.

Figure 14:
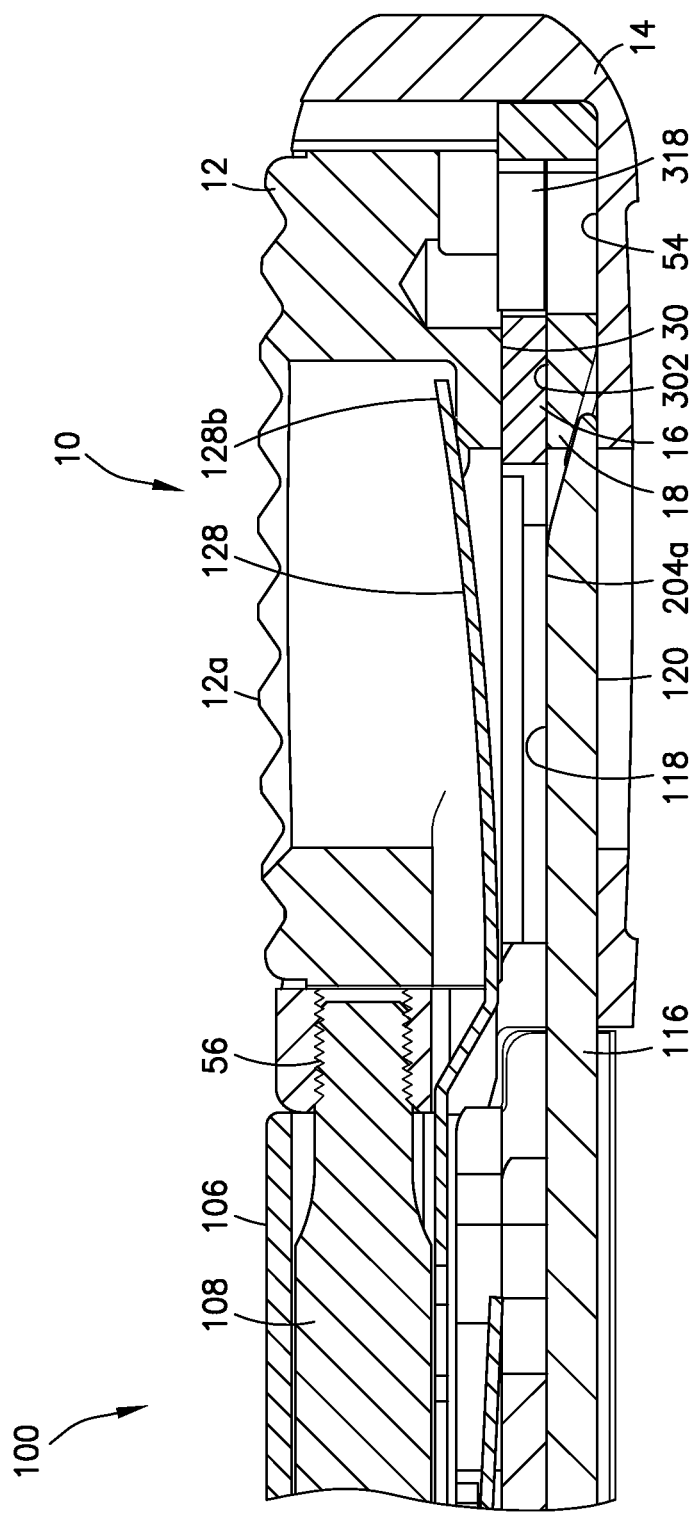
FIG. 14 is a view similar to FIG. 10a showing the first insert inserted into the expanded expandable device.
Figure 16A:
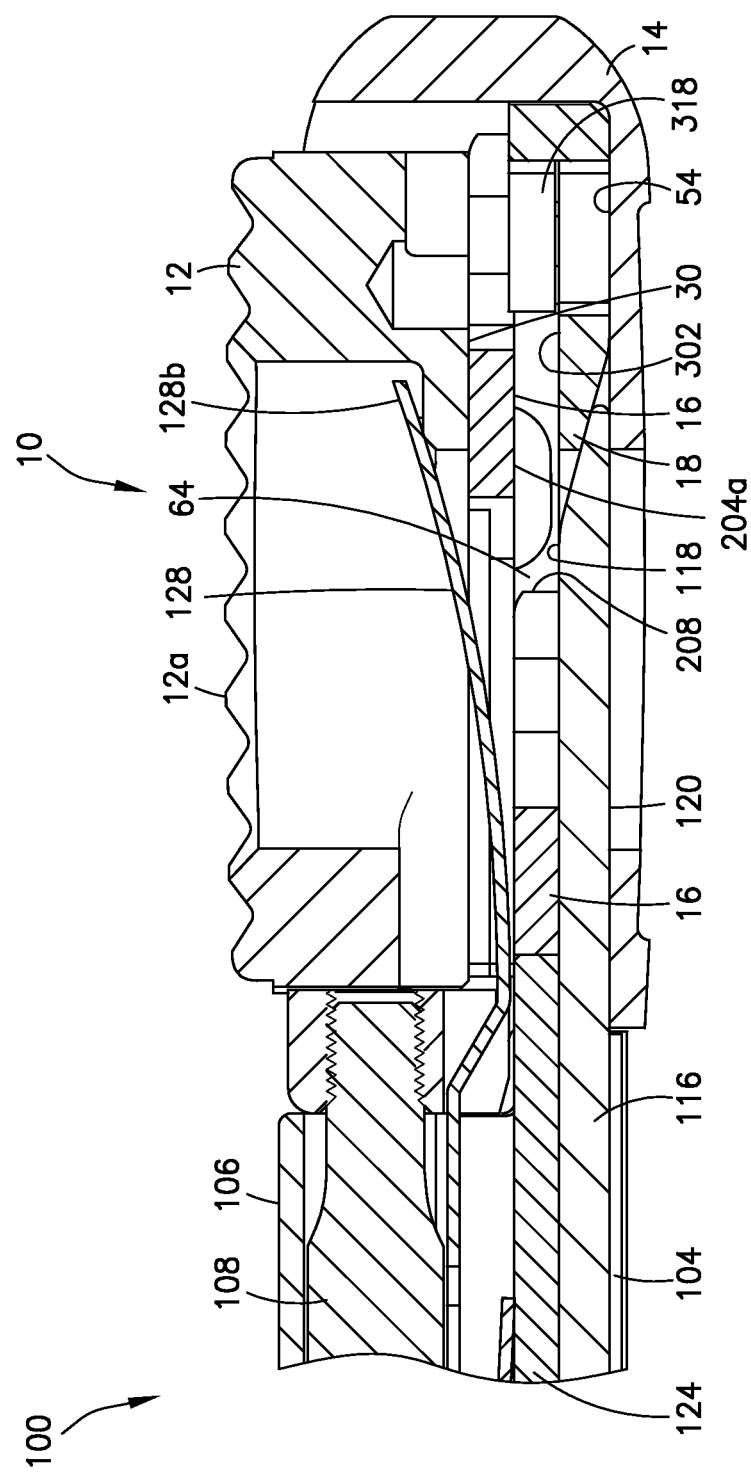
FIGS. 16a and 16b are views of the expandable device expanded as shown in the views of FIGS. 15a and 15b with the second insert having been further distally moved to a position moving the elevator away from the first insert and creating a space for the insertion of the second insert.
Figure 16B:
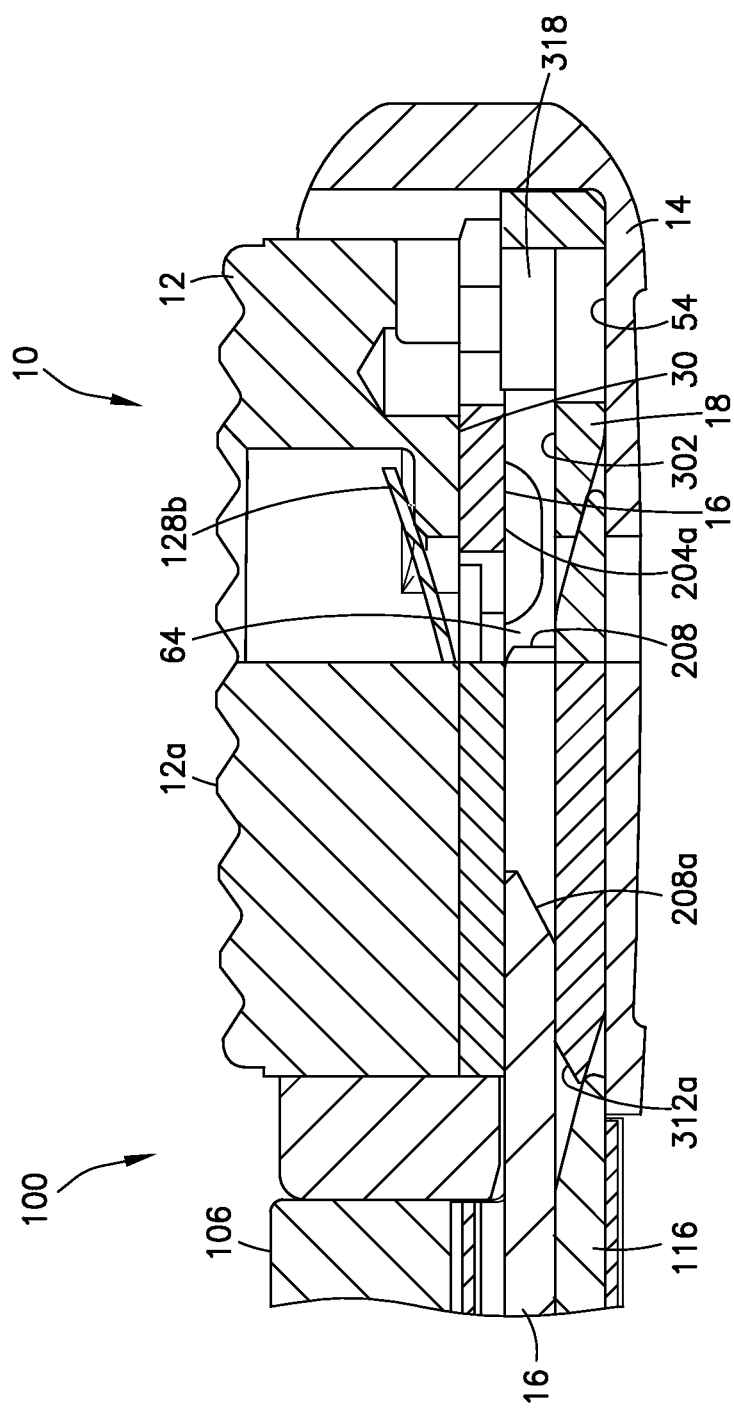

With insert 16 partially inserted in device 10, continued operation of the actuator 102 during the second stroke causes lifting platform 116 to move proximally thereby moving lifting platform 116 in a retracting direction. With distal front end 208 of insert 16 supporting superior endplate 12, continued proximal movement of lifting platform 116 causes lifting surfaces 116a, 116b and 116c of lifting platform 116 to sufficiently disengage cooperative lifting surfaces 308a, 312b, and 314b, respectively of elevator 18 to allow elevator 18 to move away in the direction of expansion from superior endplate 12 and toward inferior endplate 14 along rails 14b and return to the position of elevator 18 shown in FIGS. 10a-b. As elevator 18 returns to the position whereby the lower surface 120 of lifting platform 116 is situated on lower inner surface 54 of inferior endplate 14, a space like the space 64 as described hereinbelow with reference to FIG. 16b, is created between lower surface 30 of superior endplate 12 and upper surface 302 of elevator 18. Such space between the superior endplate 12 and the elevator 18 is slightly greater than the thickness of an insert 16 and is in direct communication with lower surface 30 of superior endplate 12 and upper surface 302 of elevator 18. During completion of the second stroke of actuator 102 driver 124 continues to move axially distally slidably pushing insert 16 fully into such space of expanded device 10, as shown in FIG. 14, with lower surface 204 of insert 16 facing and being in slidable contact with upper surface 302 of elevator 18. Driver 124 is retracted proximally to the original position shown in FIGS. 10a-b when the hand grip 134 of actuator 102 is released.

During insertion of insert 16 into device 10, receptacle 220 described hereinabove at the distal end 208 of insert 16 cooperatively receives complementary flexible latch 318 on the upper surface 302 of elevator 18 such that locking surfaces 224a, 224b and 322a, 322b resiliently interlock, as shown in FIG. 5b. Such interlocking substantially resists any back out of the insert 16 through channel 50 as driver 124 is withdrawn away from insert 16 in the retracted position. In the event device 10 is further expanded, as described hereinbelow, the initial insert 16 is moved upwardly with superior endplate 12 by elevator 18. As elevator 18 then returns downwardly toward inferior endplate 14 as will be explained, latch 318 is separated from receptacle 220 as space 64 is created. With the initial insert 16 moved upwardly, it is situated above channel 50 and held captive by the interior surfaces of inferior endplate 14, including interior surface 44a of rear end wall 44. It should be appreciated that while insert 16 is held in position within device 10 by interlocking of receptacle 220 and latch 318, other structure to resist back out movement of insert 16 may be provided, such as interlocking structure between insert 16 and one or more interior surfaces of the inferior endplate 14, or interlocking structure between adjacent inserts 16. Upon completion of insertion of insert 16, opening 216 of insert 16 is at least partially aligned with opening 316 of elevator 18, opening 38 of superior endplate 12 and opening 60 of inferior endplate 14. Once inserter 100 is removed from the expanded device upon completion of the surgical procedure, insert opening 216, elevator opening 316 and graft chambers 38 and 60, respectively, will all be in at least partial alignment and communication with each other.

Figure 15A:
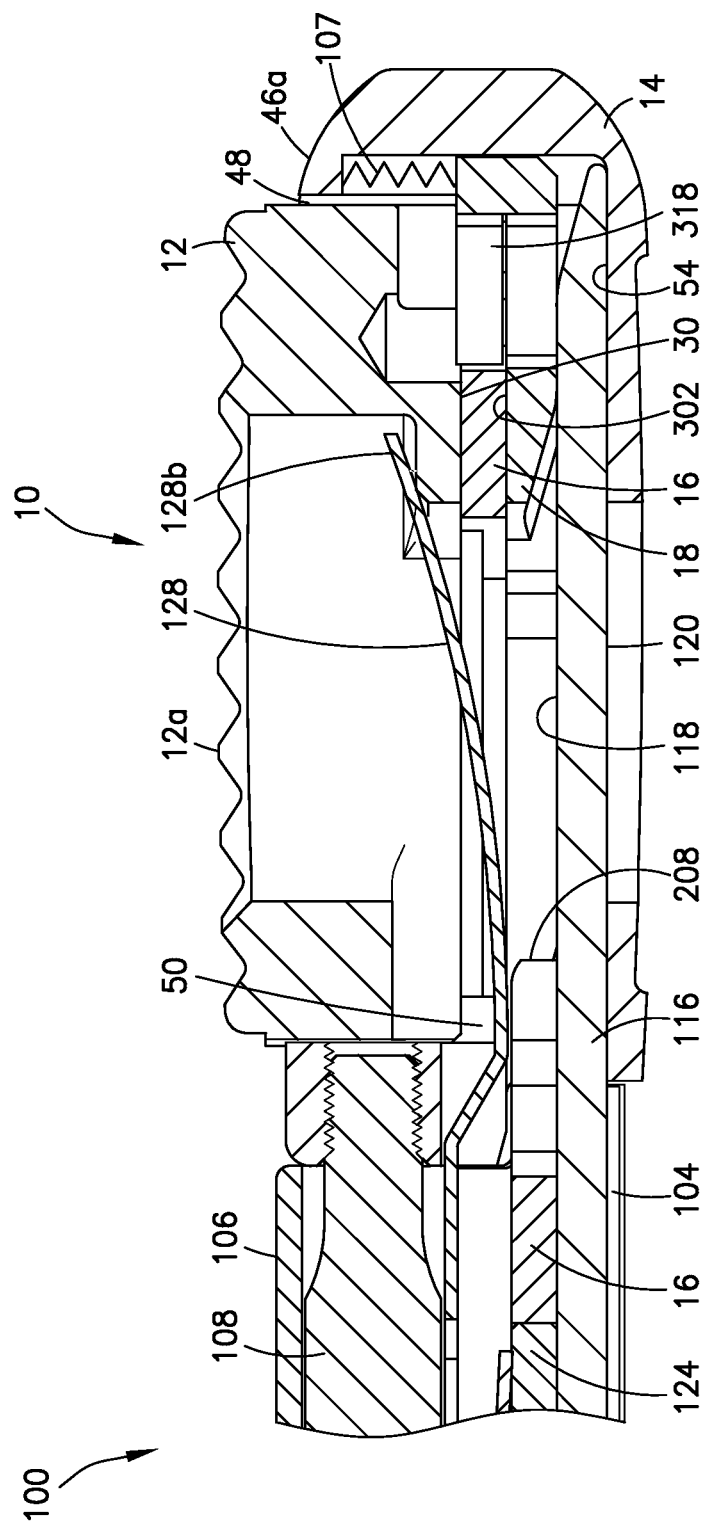
FIGS. 15a and 15b are views similar to FIGS. 13a and 13b with the lifting platform having been moved distally to a 0position lifting the elevator and the first insert to further expand the expandable device with a second insert partially entering the expanded device.
Figure 15B:
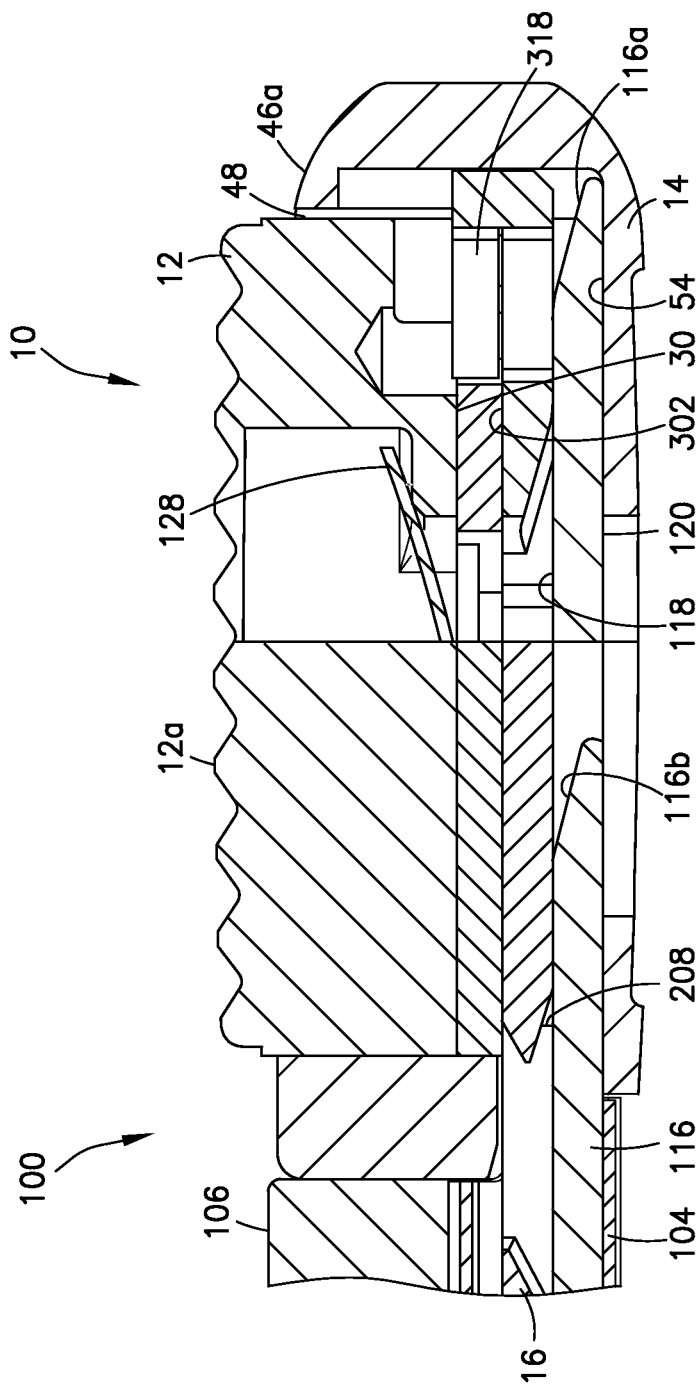

In the event the surgeon determines that additional inserts 16 are required in order to provide proper correction of the height of the intradiscal space, actuator 102 may be operated to insert one or more additional inserts 16 in the same manner as described with respect to the insertion of first insert 16. FIGS. 15a-b show device 10 with one insert 16 having been inserted and a second insert 16 partially introduced after device 10 has been further expanded during a first stroke of actuator 102 by elevator 18 upon lifting by the lifting platform 116 in the same process as described with respect to FIGS. 13a-b. As the second insert 16 enters the further expanded device 10 during the second stroke, lifting platform 116 is pulled proximally in a retracting direction, sufficiently disengaging lifting surfaces 116a, 116b and 116c of lifting platform 116 from cooperative lifting surfaces 308a, 312b, and 314b, respectively of elevator 18 to allow elevator 18 to freely return to inner surface 54 of inferior endplate 14. However, in the event elevator 18 fails to fully or partially return to such position, during pushing of second insert 16 into device 10 by driver 124, the inclined surfaces 208a adjacent the front distal end 208 of second insert 16 contacts inclined surfaces 312a and 314a, respectively at the upper free end of each arm 312 and 314 of elevator 18, as shown in FIGS. 16a-b, to urge elevator 18 toward and against lower surface 54 of the inferior endplate 14 creating a space 64 between lower surface 204 of the first insert 16 and upper surface 302 of elevator 18. Alternatively, or in addition, a suitable biasing element may be included to normally urge elevator 18 toward inner surface 54 of inferior endplate 14. Inferior endplate 14 may be formed to include a lip 46a on the front end wall 46 adjacent the distal end of cavity 48 to contain a spring 107 which would serve as the biasing element, as shown, for example, in FIG. 15a. It should be understood that the features urging elevator 18 toward lower inner surface 54 of inferior endplate 14 function during the insertion of first insert 16 as well as with all subsequently inserted inserts 16.

Figure 17:
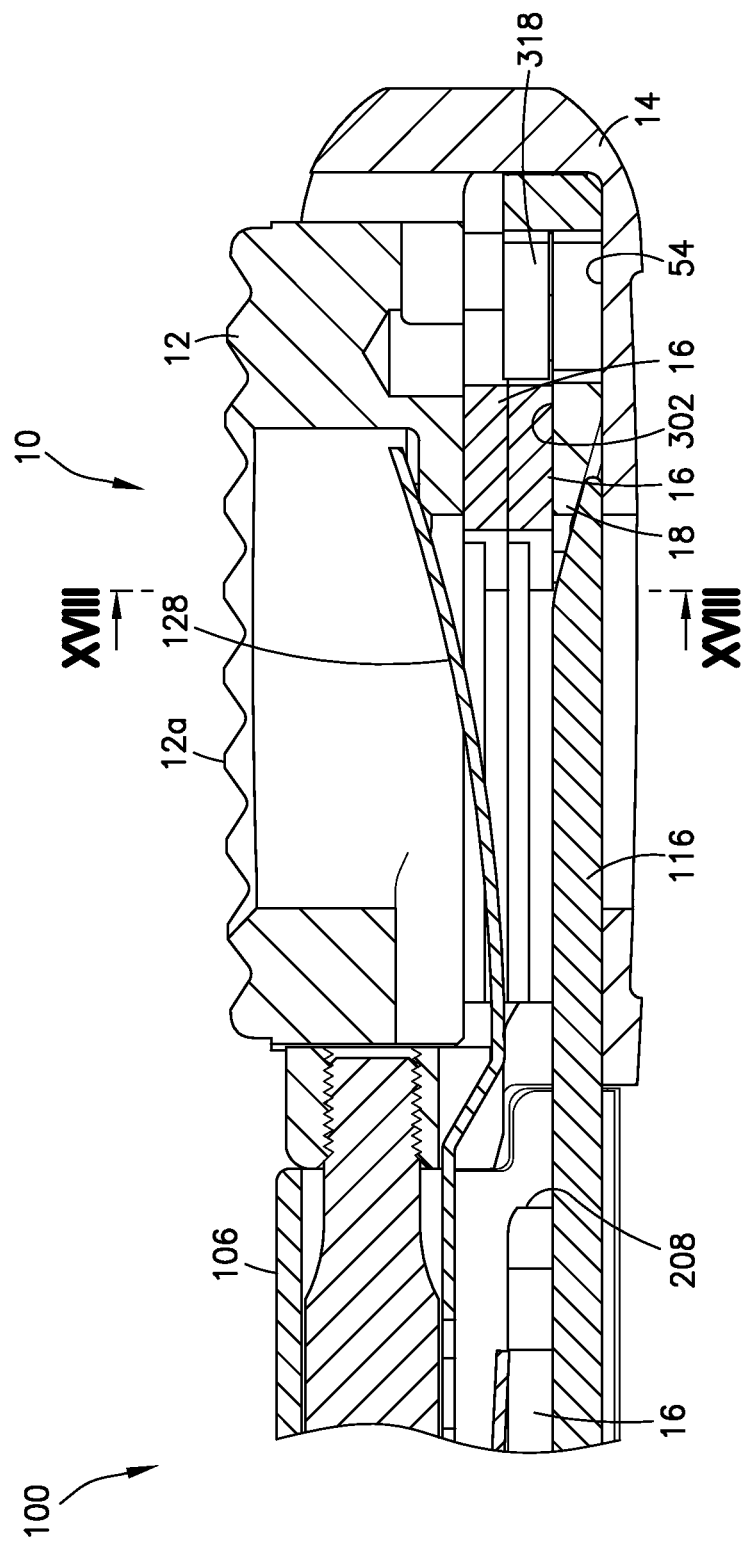
FIG. 17 is a view similar to the view of FIG. 14 showing the first and second inserts inserted into the expanded expandable device.

Continued operation of actuator 102 during the second stroke will continue to move second insert 16 until fully inserted shown in FIG. 17. During insertion of second insert 16 into device 10, the resilient interlocking features of receptacle 220 described hereinabove of the second insert 16 cooperatively interlock with the complementary interlocking features of flexible latch 318 on the distal end of elevator 18. Upon completion of insertion of second insert 16, opening 216 of insert 16 is at least partially aligned with opening 216 of the first insert, opening 38 of superior endplate 12 and opening 60 of inferior endplate 14, all of which will be in communication upon removal of inserter 100. The second insert 16 is the lowermost insert and resides on upper surface 302 of elevator 18 directly below and in contact with first insert 16, as shown in FIGS. 17 and 18. Driver 124 is then again retracted proximally to the original position shown n FIGS. 10a-b when the hand grip 134 of actuator 102 is released.

When the intradiscal space has been expanded to its maximum anatomic extent as the spine reaches ligamentotaxis and the device 10 cannot be further expanded, the surgeon will be able to determine such condition by tactile feedback. Insertion of an insert 16 into device 10 can only be achieved after elevator 18 reaches its ultimate movement in the direction of expansion toward superior endplate 12. As such, failure to compress hand grips 132/134 in a manner to complete the first stroke of actuator 102 will allow the surgeon to recognize that ligamentotaxis has been reached and the proper intradiscal height has been restored. Inasmuch as the insertion of an insert 16 follows the expansion of device 10 upon full movement of elevator 18 in the direction of expansion toward inferior endplate 14, incomplete insertion of an insert 16 may be avoided. An indication that full expansion of device 10 has been reached may also be determined visually as described hereinabove by observation that flags 162 on actuator 102 have rotated relative to frame 101. The surgeon would then terminate the procedure by actuating hex fitting 174, as described hereinabove. Inserter 100 would then be removed from the expanded device 10 by rotatably removing knob 112 from the proximal end of guide pin 108. As shown in FIG. 19, the guide pin 108 may remain releasably connected to expanded device 10 to serve as a locator for subsequent attachment to an apparatus containing suitable bone graft to assist in the delivery of such material into channel 50 of inferior endplate 14 through which inserts 16 were inserted. As such, upon removal of inserter 100 from expanded device 10, a substantially unobstructed path exists from channel 50 though opening 316 of elevator 18 and openings 216 of inserts 16 and into openings 38 and 60 extending through the superior endplate 12 and the inferior endplate 14, respectively, to allow bone graft material introduced into expanded device 10 through channel 50 to flow fully through device 10.

In accordance with certain specific applications of device 10 for posterior implantation as described hereinabove, the overall length of the device 10 as defined by the length of the inferior endplate 14 is about 25 mm. The width of the device 10 is approximately 10 mm. The height of the unexpanded device 10 of FIGS. 1a-c with the superior endplate 12 fully nested within the inferior endplate 14 is approximately 7 mm. With the introduction of five inserts 16, each of which has a thickness of approximately 1.0 mm, the height of device 10 may be expanded from an unexpanded height of approximately 7 mm to an expanded height of approximately 12 mm. It should be appreciated that these dimensions are only illustrative and the number of inserts 16 as well as the dimensions of device 10 may vary depending upon the particular surgery and application. For example, device 10 for posterior implantation may have an initial unexpanded height in the range of approximately 7-10 mm, a width in the range of approximately 10-14 mm, and a length in the range of approximately 20-35 mm, with up to eight inserts 16 for the taller sizes. For implementing such posterior-size devices 10, trigger actuator 102 may have an operating mechanism as described herein for expanding device 10 in a first stroke and fully inserting an insert 16 in a second stroke.

For certain applications of device 10 that may be implanted from a lateral approach, device 10 may have an unexpanded height in the range of approximately 8-10 mm, a width in the range of approximately 14-26 mm, and a length in the range of approximately 35-60 mm. To implant such devices 10 from the lateral approach, trigger actuator 102 may have an operating mechanism adjusted to expand device 10 in a first stroke, partially insert an insert 16 in a second stroke, and fully insert an insert 16 in a third stroke.

Channel 50, extending through the rear end wall 44, is sized and configured to facilitate the introduction of a suitable bone graft material by a graft delivery apparatus that may use guide pin 108 as a locator, as shown in FIG. 19. Such a graft delivery apparatus may have an entry tip sized and configured for entry into channel 50. In a particular arrangement, it may be desirable to increase the entry opening to further ease the delivery of graft material. In such instance, a portion of rear end wall 44 may be notched out to form a channel portion 50a of increased height directly below threaded opening 56. Channel portion 50a situated below threading opening 56 would direct the entry flow of bone graft material into the center of expanded device 10. Channel portion 50a may be suitably configured to cooperatively receive the entry tip of the graft delivery apparatus, with such channel portion 50a being rectangular, square or arcuate. In the example of device 10 for posterior applications, channel portion 50a may be particularly configured to be square. Where such device 10 has an initial unexpanded height of 7 mm and a width of 10 mm, channel portion 50a may have a width of 3 mm and a height of 3 mm as measured vertically from inner surface 54. In the example of device 10 for lateral applications, channel portion 50a may be particularly configured to be generally rectangular. Where such device 10 has an initial unexpanded height of 8 mm and a width of 16 mm, channel portion 50a may have a height of 3 mm as measured vertically from inner surface 54, and a width of 6 mm. For purposes of delivering bone graft material in the form of autograft, it is desirable that the minimum dimension of channel portion 50a, or any portion of channel 50 used as an entry port for such autograft material be no less than about 2 mm. It should be appreciated, however, that depending upon the viscosity of bone graft material to be delivered, such minimum dimension may vary.

Figure 20:
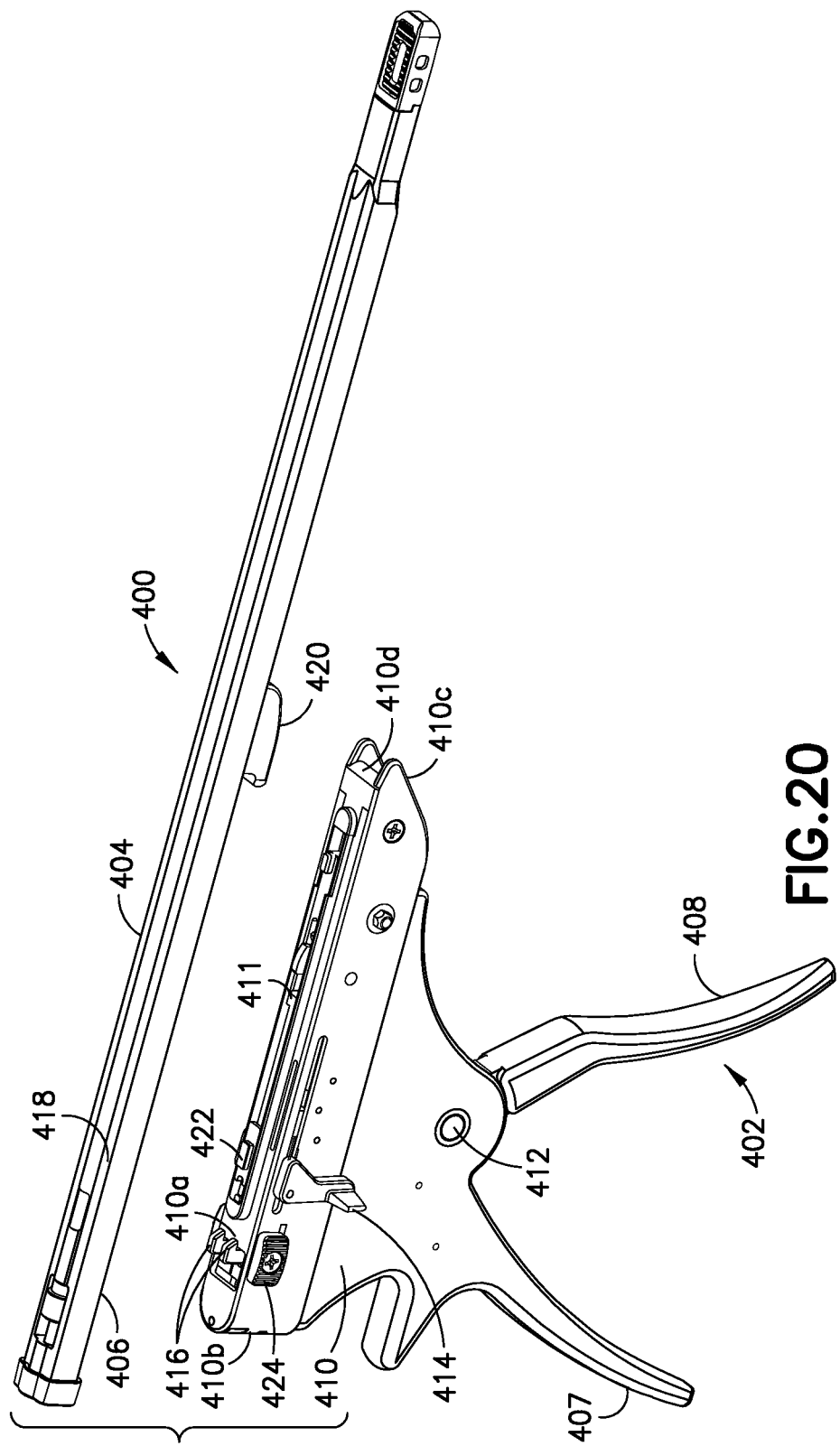
FIG. 20 is a top perspective of an apparatus including an inserter releasably attached to an expandable spinal interbody fusion device in accordance with a further embodiment of the present invention with the inserter being modular.

Turning now to FIG. 20, an alternative inserter 400 embodying a modular construction is described. Inserter 400 comprises an actuator 402 and a releasable cartridge 404. Actuator 402 includes a pair of hand grips 407 and 408 that are biased apart by an extension spring in the same manner as in trigger actuator 102 described hereinabove. Actuator 402 includes a frame 410 housing an operating mechanism 411 substantially the same as the operating mechanism of trigger actuator 102. Grip 407 is fixedly secured to frame 410 while grip 408 is pivotally connected to frame 410 by a pivot pin 412. Frame 410 supports a rotatable flag 414 that is coupled to the operating mechanism 411 as in trigger actuator 102. Frame 410 includes a pair of spring-loaded flexible latches 416 projecting upwardly from an interface surface 410a adjacent the proximal end 410b of frame 410. Adjacent the distal end 410c of frame 410 a support surface 410d is provided. Actuator 402 in a particular embodiment is reusable. Frame 410, as well as frame 101, and hand grips 407, 408, as well as hand grips 132, 134 are all formed of stainless steel in a particular arrangement, although other materials, such as aluminum alloys and plastics may also be used.

Cartridge 404 comprises a track 406 contained within an outer cover 418 similar to track 104 and cover 106 of trigger actuator 102. Cartridge 404 likewise houses a translatable lifting platform, a translatable driver and an indexing member (all not shown) that are constructed the same as lifting platform 116, driver 124 and indexing member 125 of trigger actuator 102, and that function in the same manner. A support 420 comparable to support 172 is secured to the bottom of cover 418. Cartridge 404 supports a plurality of inserts 16 in a linear array for insertion into the expandable device 10. Cooperative latching structure is provided at the bottom surface of cover 418 for releasable engagement with latches 416 of actuator 402. In a particular embodiment, cartridge 404 is disposable.

Cartridge 404 is releasably attached to frame 410 by initially engaging support 420 with support surface 410d on frame 410 and then rotating cartridge down toward proximal end 410b until latches 416 releasably attach to the cooperative latching structure at the bottom of cartridge 404. Upon attachment of cartridge 404 with actuator 402, components of operating mechanism 411 interface with the driver and the lifting mechanism within track 406 in a manner comparable to actuator 102, including the receipt of boss feature 422 (the same as boss feature 156) into a slot that is the same as slot 124d of driver 124. Cartridge 404 may be released from actuator 402 by actuation of release levers 424 supported by frame 410 on both sides thereof and movably coupled to latches 416. In all other respects, modular inserter 400 operates the same as trigger actuator 102 described hereinabove.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, an inserter with a graft shield, such as shield 128, may be used with expandable spinal interbody fusion devices having an expansion structure without an elevator 18 as described hereinabove. For example, an inserter with a graft shield 128 may be used with the expandable interbody fusion device shown and described in the '312 patent referenced hereinabove wherein the device is expanded upon introduction of a series of wafers. Shield 128 may be used similarly as described herein to provide a barrier between a graft opening through one of the endplates, such as the superior endplate, and the wafers. Such a barrier would substantially prevent bone graft material pre-packed into such opening from interfering with sliding receipt of such wafers during insertion and expansion of the device. In addition, it should also be appreciated that actuators other than trigger actuators, such as with threaded rotary mechanisms, may be used with the inserter 100 described herein.

While one use of the invention as described herein is as an expandable spinal interbody fusion device, the invention may also be used in any situation where it is desirable to expand two tissue surfaces and to support such tissue surfaces after they have been separated. The tissue may be bone, skin, soft tissue, or combinations thereof. Further, the surfaces may be opposed surfaces of contiguous elements or surfaces of opposed elements. Thus, in addition to being used as a spinal interbody fusion device as set forth herein, the invention may also be used to treat vertebral compression fractures, for replacement of vertebral bodies (VBR), as a wedge opening high tibial osteotomy, tibial tuberosity elevation, as well as for treating other compression fractures including, but not limited to tibia plateau fractures, calcaneous, distal tibial fractures, or distal radius (wrist) fractures. One method for treating these conditions includes distracting and supporting the tissue surfaces simultaneously, as described in the '998 patent. The approach described herein, which includes expanding the tissue and then supporting the expanded tissue, may be used to treat these same conditions.

Such procedures may be performed percutaneously through a cannula or other minimally invasive instrument or in an open procedure.

Figure 21:
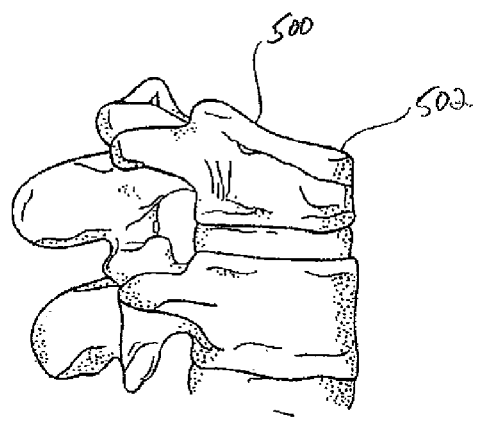
FIG. 21 shows a vertebral body having a compression fracture displacing its superior and anterior edge.
Figure 22:
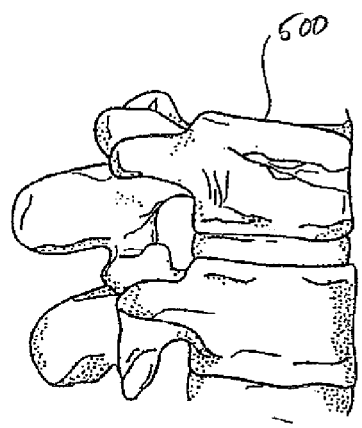
FIG. 22 shows a vertebral body, following treatment of a compression fracture.
Figure 23:
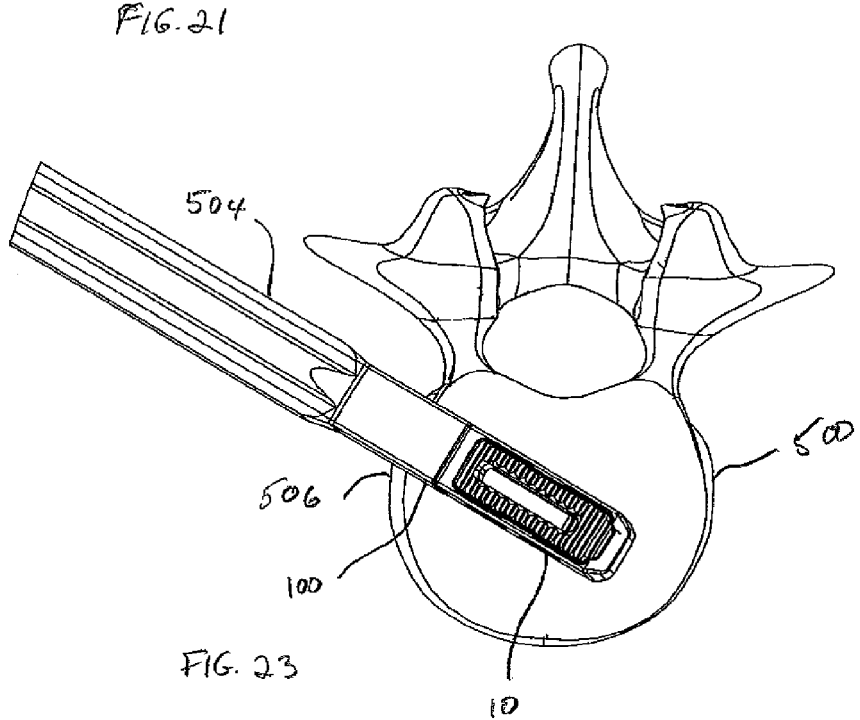
FIG. 23 illustrates a plan view of an insertion apparatus according to another embodiment of the invention, placed within a vertebral body of FIG. 21, shown in cross-section.

The expansion device is now described in this section by its application as a spinal implant to vertebral compression fractures. FIG. 21 shows a vertebral body 500 having a compression fracture displacing its superior and anterior edge 502. FIG. 22 shows vertebral body 500 wherein the height has been restored. FIG. 23 illustrates an extrapedicular approach to vertebral body 500 wherein an access cannula 504 is placed through the posterolateral wall 506 of vertebral body 500. Other approaches may optionally be used for placing a cannula into a vertebral body such as a transpedicular approach to the vertebral body wherein an access cannula may be placed through the pedicle. In the extrapedicular approach, two cannulae 504 may be placed bilaterally, one on each side.

Figure 24:
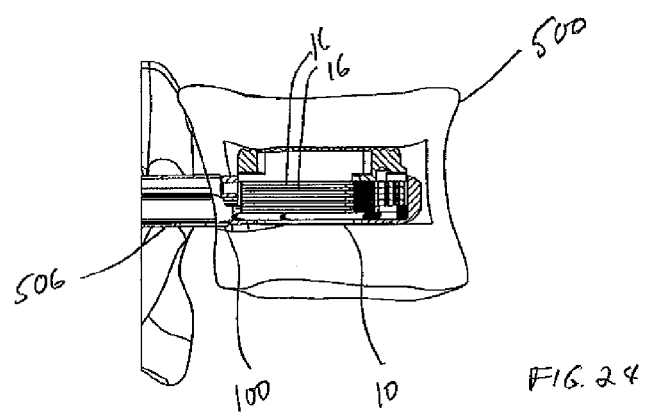
FIG. 24 shows a side view of the insertion apparatus of FIG. 23 being deployed within a vertebral body, shown in sectional view.

The procedure for the placement of access cannula 504 into verterbral body 500 is more fully described in the '998 patent, incorporated herein by reference. Cannula 504 in this particular arrangement is preferably rectangular in cross-section, although cannulae of other cross-sections, such as circular may be used. Further, cannula 504 may be of fixed configuration or expandable. Once access cannula 504 is in place, an expandable device 10 supported by inserter 100 may be introduced into vertebral body 500 through cannula 504. This application of the invention contemplates expanding expandable device 10 by the inserter 100 from an unexpanded condition as shown, for example in FIG. 3a to the expanded height as shown in FIG. 24 to ultimately reduce the vertebral compression fracture and substantially restore the normal anatomic height of vertebral body 500, inserting one or more inserts, such as inserts 16, as described herein, to form a stack of inserts 16 between the expanded superior endplate 12 and inferior endplate 14 of expandable device 10. In the particular arrangement being described for vertebral compression fracture reduction, expandable device 10 may have a length of approximately 25 mm, a width of approximately 10 mm, and an unexpanded height H of approximately 7 mm. The height H may be expanded by 5 mm and supported by the introduction of five inserts 16, as shown in FIG. 24, each insert 16 as described herein having a thickness of 1 mm. It should be appreciated that the height H may be increased by other amounts and more or less than five inserts used, and that device 10 may be configured in other dimensions as set forth in the '998 patent.

When the fracture is reduced as depicted in FIG. 22, or when the physician determines that an adequate number of inserts 16 has been inserted, the inserter 100 may be 'separated from device 10 and removed from cannula 504 while expanded device 10 remains within vertebral body 500. Access cannula 504 is left in place. Suitable bone filler may be injected into vertebral body 500 through cannula 504 to encapsulate device 10, provide weight bearing structure and increase stability of vertebral body 500. Bone filler may flow through device 10 and the insert column and out to the surrounding bone to interdigitate with cancellous bone.

It should therefore be understood that while various embodiments of the invention have been presented herein, various changes, modifications and further applications may be made without departing from the spirit of the invention and the scope of the appended claims.

What is claimed is:

1. An expandable device for implantation between two opposing tissue surfaces of a body, comprising:
    an inferior endplate having an outer surface configured to contact one body tissue surface;
    a superior endplate having an outer surface configured to contact an opposing body tissue surface, said inferior endplate and said superior endplate being movable relative to each other in a direction of expansion; and
    an elevator inseparably disposed in said device between said inferior endplate and said superior endplate, said elevator being captively retained prior to expansion of the device for independent movement in a first direction toward said superior endplate during expansion and in a second direction away from said superior endplate after expansion to create a space between said superior endplate and said elevator.

2. The device of claim 1, wherein said elevator comprises a lifting surface for contact with an external instrument for movement of said elevator.

3. The device of claim 2, wherein said lifting surface comprises multiple contact points.

4. The device of claim 3, wherein said elevator is elongate and generally flat and has a distal end and a proximal end, an upper surface facing said superior endplate and a lower surface facing and supported by said inferior endplate.

5. The device of claim 4, wherein said elevator comprises a lifting surface adjacent said distal end and a lifting surface adjacent said proximal end.

6. An expandable device for implantation between two opposing tissue surfaces of a body, comprising:
    an inferior endplate having an outer surface configured to contact one body tissue surface;
    a superior endplate having an outer surface configured to contact an opposing body tissue surface, said inferior endplate and said superior endplate being movable relative to each other in a direction of expansion; and
    an elevator disposed between said inferior endplate and said superior endplate, said elevator being captively retained prior to expansion of the device for independent movement in a first direction toward said superior endplate during expansion and in a second direction away from said superior endplate after expansion to create a space between said superior endplate and said elevator, said elevator being elongate and generally flat and having a distal end and a proximal end, an upper surface facing said superior endplate and a lower surface facing and supported by said inferior endplate, said elevator comprising a substantially U-shaped configuration with a pair of opposing arms defining an opening through said upper surface, said lower surface and said proximal end.

7. The device of claim 6, wherein said elevator comprises a lifting surface adjacent the proximal end of each arm defining with the lifting surface adjacent the distal end at least three points contact.

8. The device of claim 7, wherein each of said lifting surfaces of said elevator is formed as an inclined ramp communicating with the lower surface of said elevator.

9. The device of claim 2, wherein said inferior endplate comprises interior surfaces constraining movement of said elevator in directions transverse to said direction of expansion and allowing movement of said elevator in the direction of expansion.

10. An expandable device for implantation between two opposing tissue surfaces of a body, comprising:
    an inferior endplate having an outer surface configured to contact one body tissue surface;
    a superior endplate having an outer surface configured to contact an opposing body tissue surface, said inferior endplate and said superior endplate being movable relative to each other in a direction of expansion;

an elevator captively retained prior to expansion of said device for independent movement along the direction of expansion between said inferior endplate and said superior endplate, said elevator being moveable in a first direction during expansion toward said superior endplate to move said superior endplate away from said inferior endplate and thereby expand said device, and in a second opposite direction after expansion toward said inferior endplate to create a space between said superior endplate and said elevator for receipt of an insert; and at least one insert in said space between said superior endplate and said elevator created by the movement of said elevator.

11. The device of claim 10, wherein said inferior endplate comprises an interior support surface supporting said elevator thereon, said elevator being elongate and generally flat having a distal end, a proximal end, and upper surface and a lower surface, said support surface of said inferior endplate contacting the lower surface of said elevator.

12. The device of claim 11, wherein said at least one insert is elongate and generally flat having a distal end, a proximal end, an upper surface, and a lower surface, the lower surface of said at least one insert facing and being in contact with upper surface of said elevator.

13. The device of claim 12, wherein said superior endplate has an opening extending through said outer surface and said lower surface, said inferior endplate has an opening extending through said outer surface and said support surface, said at least one insert has an opening through said upper surface and said lower surface, and said elevator has an opening through said upper surface and said lower surface, the openings through said superior endplate, said inferior endplate, said at least one insert and said elevator being generally aligned and in communication in the direction of expansion.

14. The device of claim 13, wherein said elevator comprises a substantially U-shaped configuration and includes a pair of opposing arms, said opening of said elevator being defined by said opposing arms and extending through the proximal end of said elevator.

15. The device of claim 14, wherein said at least one insert comprises a substantially U-shaped configuration including a pair of opposing arms, said opening through said at least one insert being defined by said opposing arms and extending through the proximal end of said at least one insert.

16. The device of claim 15, wherein said elevator comprises a lifting surface adjacent said distal end and a lifting surface adjacent said proximal end.

17. The device of claim 16, wherein said elevator comprises a lifting surface on the proximal end of each arm defining with the lifting surface adjacent the distal end at least three points contact.

18. The device of claim 17, wherein said inferior endplate comprises interior surfaces constraining movement of said elevator in directions transverse to said direction of expansion and allowing movement of said elevator in the direction of expansion.

19. The device of claim 11, wherein said inferior endplate further includes a biasing element to normally urge said elevator toward interior surface of said inferior endplate.

20. The device of claim 10, wherein said at least one insert comprises an inclined surface adjacent the distal end of said at least one insert communicating with the lower surface of said at least one insert for contacting the elevator adjacent the proximal end thereof for urging said elevator toward said inferior endplate during insertion of said insert.

21. The device of claim 10, wherein said elevator and said at least one insert each has a thickness in the direction of expansion, the thickness of said elevator being slightly greater than the thickness of said at least one insert.

22. An expandable device for implantation between two opposing tissue surfaces of a body, comprising:

a superior endplate having an outer surface configured to contact one body tissue surface, an opposite lower surface and a graft opening extending through said outer surface and said lower surface;

an inferior endplate having an outer surface configured to contact an opposing body tissue surface and an inner support surface, said inferior endplate having opposing spaced apart sidewalls and opposing spaced apart distal and proximal endwalls defining therewithin an interior cavity, said inner support surface being within said interior cavity, said superior endplate being received within said interior cavity, said inferior endplate having a graft opening extending through said outer surface and said inner support surface and communicating with said interior cavity, said rear endwall defining therethrough a channel in communication with said interior cavity, said inferior endplate being movable in a direction of expansion relative to said superior endplate toward the opposing vertebral body;

a first insert received through said channel into said interior cavity, said first insert being in contact with said superior endplate and having an opening therethrough in at least partial alignment and communication with said graft opening through said superior endplate; and an elevator supported by said inner support surface of said inferior endplate and supporting said first insert, said elevator being movable in a first direction along the direction of expansion to move said first insert and thereby said superior endplate away from said inferior endplate and thereby expand said device, and in a second opposite direction away from said first insert and toward said inferior endplate along the direction of expansion after expansion of said device to create a space between said first insert and said elevator for receipt of a second insert.

23. The device of claim 22, wherein said elevator is captively supported within said interior cavity and slidably movable in the direction of expansion, said elevator being generally flat and having a distal end and a proximal end, a lifting surface adjacent said distal end and a lifting surface adjacent said proximal end.

24. The device of claim 23, wherein said elevator comprises a substantially U-shaped configuration and including a pair of opposing arms, said opening of said elevator being defined by said opposing arms and extending through the proximal end of said elevator.

25. The device of claim 24, wherein said first insert is generally flat having a distal end and a proximal end, said first insert being of generally U-shaped configuration including a pair of opposing arms, said opening through said first insert being defined by said opposing arms and extending through the proximal end of said first insert.

26. The device of claim 23, wherein said graft opening of said superior endplate, said graft opening of said inferior endplate, and said openings through said first insert and said elevator are in at least partial alignment and in communication with each other and said channel, thereby providing a substantially unobstructed path from said channel through said device and into said graft openings of said superior and inferior endplates.

27. An expandable device for implantation between two opposing tissue surfaces of a body, comprising:
- an inferior endplate having an outer surface configured to contact one body tissue surface and an interior surface defining a cavity having a lower inner support surface;
- a superior endplate having an outer surface configured to contact an opposing body tissue surface, said inferior endplate and said superior endplate being movable relative to each other in a direction of expansion;
- an elevator disposed within said cavity between said lower inner support surface of inferior endplate and said superior endplate, said elevator being captively retained within said device prior to expansion and supported by a portion of said interior surface of said inferior endplate for independent movement in a first direction during expansion toward said superior endplate and in a second direction after expansion away from said superior endplate; and
- an insert slidably received in said cavity between said superior endplate and said elevator in a direction of introduction transverse to the direction of expansion, said insert including a surface to resist movement of said insert upon receipt within said cavity in a direction generally opposite said direction of introduction.

28. The device of claim 27, wherein said surface of said insert to resist movement comprises a portion cooperatively engaging a portion of said elevator.

29. The device of claim 28, wherein said interior surface of said inferior endplate comprises a rail projecting into said cavity and extending in the direction of expansion.

30. The device of claim 29, wherein said elevator has a recessed surface in sliding engagement with said rail to captively support said elevator within said cavity and allow independent sliding movement of said elevator in said first and said second directions within said cavity.

31. The device of claim 1, wherein said expandable device is a spinal implant.

32. The device if claim 31, wherein said spinal implant is an implant for the treatment of vertebral compression fractures.

33. The device of claim 31, wherein said spinal implant is an interbody fusion device for implantation into the intradiscal space between two opposing vertebral bodies of a spine.

* * * * *